(12) United States Patent
Chong et al.

(10) Patent No.: US 8,998,858 B2
(45) Date of Patent: Apr. 7, 2015

(54) ALIGNMENT AND CONNECTION SYSTEMS AND METHODS

(75) Inventors: Colin A. Chong, Burbank, CA (US); Rafael Bikovsky, Oak Park, CA (US); Neil Andre Quitoviera, Granada Hills, CA (US); Arsen Ibranyan, Glendale, CA (US); Matthew William Yavorsky, Los Angeles, CA (US); Mona-Lisa Alexander, San Marino, CA (US)

(73) Assignee: Medtronic Minimed, Inc., Northridge, CA (US)

( * ) Notice: Subject to any disclaimer, the term of this patent is extended or adjusted under 35 U.S.C. 154(b) by 292 days.

(21) Appl. No.: 12/974,106

(22) Filed: Dec. 21, 2010

(65) Prior Publication Data

US 2011/0160678 A1 Jun. 30, 2011

Related U.S. Application Data

(63) Continuation-in-part of application No. 12/649,172, filed on Dec. 29, 2009, and a continuation-in-part of application No. 12/650,287, filed on Dec. 30, 2009, and a continuation-in-part of application No. 12/649,619, filed on Dec. 30, 2009, and a continuation-in-part of application No. 12/650,378, filed on Dec. 30, 2009.

(51) Int. Cl.
*A61M 5/00* (2006.01)
*A61M 5/142* (2006.01)
(Continued)

(52) U.S. Cl.
CPC ......... *A61M 5/14248* (2013.01); *A61M 5/1413* (2013.01); *A61M 5/1456* (2013.01);
(Continued)

(58) Field of Classification Search
CPC .............. A61M 5/1413; A61M 39/10; A61M 39/1011; A61M 39/14; A61M 2039/10; A61M 2039/1066; A61M 2039/1072
USPC ................ 604/93.01, 64, 131, 165, 152, 905, 604/87–89, 244, 256
See application file for complete search history.

(56) References Cited

U.S. PATENT DOCUMENTS 3,701,345 A 10/1972 Heilman et al.
3,884,230 A 5/1975 Wulff
(Continued)

FOREIGN PATENT DOCUMENTS

DE 3144825 5/1983
EP 0092712 11/1983
(Continued)

OTHER PUBLICATIONS

Search Report dated Jul. 13, 2011 from related PCT application No. PCT/US2010/060895.
(Continued)

*Primary Examiner* — Laura Bouchelle
(74) *Attorney, Agent, or Firm* — Foley & Lardner LLP

(57) ABSTRACT

A connecting structure for connecting a first member in fluid flow connection with a second member may include a receptacle structure provided on the first member and having an interior chamber and an opening into the interior chamber in which a needle and a pierceable member surrounding a piercing end of the needle may be supported. The second member may include a connection portion that has a septum supported in an interior chamber having a size and shape suitable to be received at least partially into the opening of the receptacle structure upon moving the first member and the second member together to push the pierceable member toward the piercing end of the needle to cause the piercing end of the needle to pierce the pierceable member and the septum to come into fluid flow communication with the interior chamber of the connection portion.

39 Claims, 20 Drawing Sheets

(51) Int. Cl.
*A61M 5/14* (2006.01)
*A61M 5/158* (2006.01)
*A61M 5/145* (2006.01)
*A61M 5/172* (2006.01)
*A61M 39/10* (2006.01)

(52) U.S. Cl.
CPC ............ *A61M 5/158* (2013.01); *A61M 5/1723* (2013.01); *A61M 2005/14252* (2013.01); *A61M 2005/14268* (2013.01); *A61M 2005/1583* (2013.01); *A61M 2005/1585* (2013.01); *A61M 2039/1066* (2013.01); *A61M 2039/1072* (2013.01); *A61M 2209/045* (2013.01); *A61M 2230/201* (2013.01); *Y10S 604/905* (2013.01)

(56) References Cited

U.S. PATENT DOCUMENTS

| | | | |
|---|---|---|---|
| 3,994,295 | A | 11/1976 | Wulff |
| 4,633,232 | A | 12/1986 | Nelson et al. |
| 5,122,123 | A | 6/1992 | Vaillancourt |
| 5,176,662 | A | 1/1993 | Bartholomew et al. |
| 5,236,416 | A | 8/1993 | McDaniel et al. |
| 5,334,188 | A * | 8/1994 | Inoue et al. .................... 604/539 |
| 5,533,981 | A | 7/1996 | Mandro et al. |
| 5,628,309 | A | 5/1997 | Brown |
| 5,662,612 | A | 9/1997 | Niehoff |
| 5,954,697 | A | 9/1999 | Srisathapat et al. |
| 6,283,943 | B1 | 9/2001 | Dy et al. |
| 6,299,131 | B1 * | 10/2001 | Ryan .......................... 251/149.1 |
| 6,423,035 | B1 | 7/2002 | Das et al. |
| 6,461,329 | B1 | 10/2002 | Van Antwerp et al. |
| 6,699,218 | B2 | 3/2004 | Flaherty et al. |
| 6,727,689 | B1 | 4/2004 | Furlong et al. |
| 6,740,059 | B2 | 5/2004 | Flaherty |
| 6,749,587 | B2 | 6/2004 | Flaherty |
| 6,945,760 | B2 | 9/2005 | Gray et al. |
| 6,960,192 | B1 | 11/2005 | Flaherty et al. |
| 7,018,360 | B2 | 3/2006 | Flaherty et al. |
| 7,396,353 | B2 * | 7/2008 | Lorenzen et al. .......... 604/891.1 |
| 8,152,771 | B2 | 4/2012 | Mogensen et al. |
| 8,308,679 | B2 | 11/2012 | Hanson et al. |
| 8,435,209 | B2 | 5/2013 | Hanson et al. |
| 2001/0034506 | A1 | 10/2001 | Hirschman et al. |
| 2001/0041869 | A1 | 11/2001 | Causey et al. |
| 2004/0002682 | A1 | 1/2004 | Kovelman et al. |
| 2004/0162521 | A1 | 8/2004 | Bengtsson |
| 2005/0065472 | A1 | 3/2005 | Cindrich et al. |
| 2005/0101932 | A1 | 5/2005 | Cote et al. |
| 2006/0061353 | A1 | 3/2006 | Etherington et al. |
| 2006/0079765 | A1 | 4/2006 | Neer et al. |
| 2006/0200020 | A1 | 9/2006 | Brister et al. |
| 2007/0049865 | A1 | 3/2007 | Radmer et al. |
| 2007/0060871 | A1 | 3/2007 | Istoc et al. |
| 2007/0073236 | A1 | 3/2007 | Mernoe et al. |
| 2007/0191702 | A1 | 8/2007 | Yodfat et al. |
| 2007/0191770 | A1 | 8/2007 | Moberg et al. |
| 2007/0270744 | A1 | 11/2007 | Dacquay et al. |
| 2008/0051697 | A1 | 2/2008 | Mounce et al. |
| 2008/0051711 | A1 | 2/2008 | Mounce et al. |
| 2008/0051714 | A1 * | 2/2008 | Moberg et al. ................. 604/135 |
| 2008/0097321 | A1 * | 4/2008 | Mounce et al. ............... 604/132 |
| 2008/0097381 | A1 | 4/2008 | Moberg et al. |
| 2008/0269687 | A1 | 10/2008 | Chong et al. |
| 2008/0281270 | A1 | 11/2008 | Cross et al. |
| 2008/0319414 | A1 | 12/2008 | Yodfat et al. |
| 2009/0069750 | A1 | 3/2009 | Schraga |
| 2009/0156990 | A1 | 6/2009 | Wenger et al. |
| 2009/0182301 | A1 * | 7/2009 | Bassarab et al. ............. 604/416 |
| 2009/0259183 | A1 | 10/2009 | Chong et al. |
| 2009/0259198 | A1 | 10/2009 | Chong et al. |
| 2009/0264825 | A1 | 10/2009 | Cote |
| 2009/0326458 | A1 | 12/2009 | Chong et al. |
| 2010/0137790 | A1 | 6/2010 | Yodfat |
| 2010/0152658 | A1 | 6/2010 | Hanson et al. |
| 2010/0274180 | A1 | 10/2010 | Donovan et al. |
| 2011/0166512 | A1 | 7/2011 | Both et al. |
| 2011/0178461 | A1 | 7/2011 | Chong et al. |
| 2011/0213306 | A1 | 9/2011 | Hanson et al. |
| 2012/0215163 | A1 | 8/2012 | Hanson et al. |
| 2013/0253422 | A1 | 9/2013 | Hanson et al. |

FOREIGN PATENT DOCUMENTS

| | | |
|---|---|---|
| EP | 0317808 | 5/1989 |
| EP | 0 937 475 | 8/1999 |
| EP | 1177802 | 2/2002 |
| EP | 1752172 | 2/2007 |
| EP | 2 077 128 B1 | 12/2010 |
| GB | 2 327 151 | 1/1999 |
| JP | 11-339439 | 12/1999 |
| WO | WO-86/02562 | 5/1986 |
| WO | WO-99/33504 | 7/1999 |
| WO | WO-00/47254 | 8/2000 |
| WO | WO-01/68163 | 9/2001 |
| WO | WO-2006/031500 | 3/2006 |
| WO | WO-2006/076656 | 7/2006 |
| WO | WO-2006/121921 A2 | 11/2006 |
| WO | WO-2006/122406 | 11/2006 |
| WO | WO-2006/124756 | 11/2006 |
| WO | WO-2008/024810 | 2/2008 |
| WO | WO-2008/024812 A2 | 2/2008 |
| WO | WO-2008/024814 A2 | 2/2008 |
| WO | WO-2008/078318 | 7/2008 |
| WO | WO-2008/092782 | 8/2008 |
| WO | WO-2008/133702 A1 | 11/2008 |
| WO | WO-2009/001346 | 12/2008 |
| WO | WO-2009/016638 | 2/2009 |
| WO | WO-2009/033032 A1 | 3/2009 |
| WO | WO-2009/066288 | 5/2009 |
| WO | WO-2009/093759 A1 | 7/2009 |
| WO | WO-2009/098291 A1 | 8/2009 |
| WO | WO-2009/106517 | 9/2009 |
| WO | WO-2009/125398 A2 | 10/2009 |
| WO | WO-2009/135667 | 11/2009 |
| WO | WO-2009/144726 A1 | 12/2009 |
| WO | WO-2010/042814 | 4/2010 |
| WO | WO-2011-082256 | 7/2011 |
| WO | WO-2011/090629 | 7/2011 |
| WO | WO-2011/119768 | 9/2011 |

OTHER PUBLICATIONS

Partial Search Report dated Mar. 1, 2011 from related patent application No. PCT/US2010/060892.
Partial Search Report dated Mar. 21, 2011 from related patent application No. PCT/US2010/060895.
Partial Search Report dated Mar. 23, 2011 from related patent application No. PCT/US2010/047590.
US Office Action dated Mar. 3, 2011 from related U.S. Appl. No. 12/649,172.
US Office Action dated Oct. 7, 2010 from related U.S. Appl. No. 12/649,172.
International Search Report and Written Opinion from related patent application No. PCT/US2010/062414.
IPRP dated Mar. 6, 2012 from related PCT/US2010/047590 application.
International Search Report and Written Opinion from related PCT application No. PCT/US2011/066501, mailed Dec. 12, 2012, 23 pages.
International Search Report and Written Opinion from related PCT application No. PCT/US2011/066504, mailed Oct. 24, 2012, 29 pages.
International Search Report and Written Opinion from related PCT application No. PCT/US2012/022881, mailed Aug. 28, 2012, 21 pages.
International Search Report and Written Opinion from related PCT application No. PCT/US2012/022883, mailed Aug. 7, 2012, 21 pages.
International Search Report and Written Opinion from related PCT application No. PCT/US2012/055661, mailed Dec. 11, 2012, 11 pages.

(56) References Cited

OTHER PUBLICATIONS

U.S. Notice of Allowance from related U.S. Appl. No. 13/235,228, mailed Dec. 20, 2012, 12 pages.
U.S. Non-Final Office Action from related U.S. Appl. No. 12/553,038, mailed Dec. 28, 2012, 10 pages.
Partial International Search Report from related PCT application No. PCT/US2012/064454, mailed Feb. 4, 2013, 5 pages.
U.S. Office Action from related U.S. Appl. No. 12/553,038, mailed Jun. 20, 2013.
U.S. Office Action from related U.S. Appl. No. 13/103,014, mailed May 22, 2013.
International Search Report and Written Opinion from related PCT application No. PCT/US2012/064454, mailed Jun. 12, 2013.
Japanese Office Action from related Japanese Patent Application No. 2012-528022, issued Mar. 25, 2014, 3 pages.
US Notice of Allowance dated Jul. 7, 2014, from related U.S. Appl. No. 12/650,287.
US Office Action dated Jun. 24, 2014, from related U.S. Appl. No. 12/649,172.
US Notice of Allowance dated Jul. 24, 2014, from related U.S. Appl. No. 13/015,028.
U.S. Office Action dated Sep. 5, 2014, from related U.S. Appl. No. 12/650,378.
U.S. Notice of Allowance dated Sep. 22, 2014, from related U.S. Appl. No. 13/015,051.
U.S. Office Action dated Sep. 11, 2014, from related U.S. Appl. No. 13/462,752.
U.S. Office Action dated Sep. 8, 2014, from related U.S. Appl. No. 13/421,564.
U.S. Office Action dated Oct. 9, 2014, from related U.S. Appl. No. 12/974,117.
U.S. Office Action dated Jan. 9, 2015, from related U.S. Appl. No. 12/649,172.

* cited by examiner

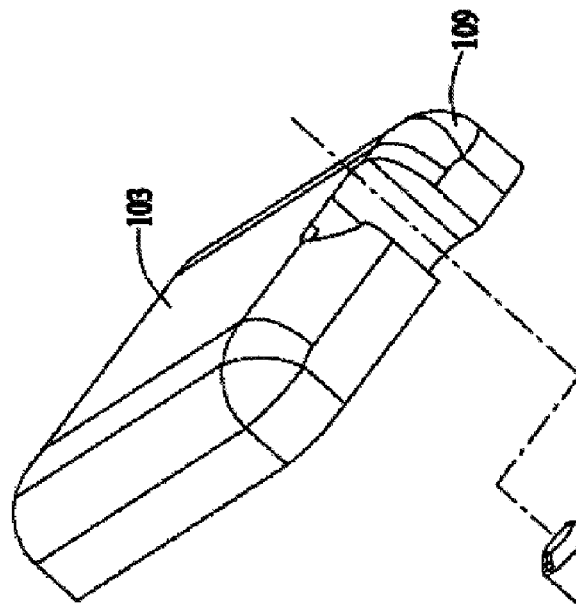
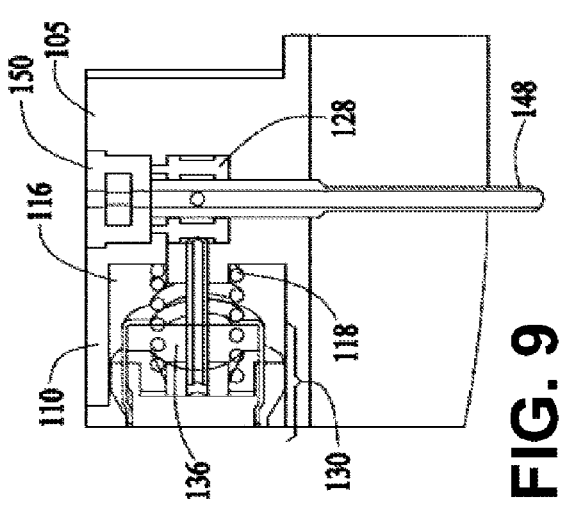
FIG. 10
FIG. 9

ALIGNMENT AND CONNECTION SYSTEMS AND METHODS

CROSS-REFERENCE TO RELATED PATENT APPLICATIONS

This application is a Continuation-In-Part of U.S. application Ser. No. 12/649,172, filed Dec. 29, 2009, incorporated herein by reference in its entirety. This application is a Continuation-In-Part of U.S. application Ser. No. 12/650,378, filed Dec. 30, 2009, incorporated herein by reference in its entirety. This application is a Continuation-In-Part of U.S. application Ser. No. 12/649,619, filed Dec. 30, 2009, incorporated herein by reference in its entirety. This application is a Continuation-In-Part of U.S. application Ser. No. 12/650,287, filed Dec. 30, 2009, incorporated herein by reference in its entirety.

BACKGROUND

1. Field of the Invention

Embodiments of the present invention generally relate to alignment and/or connection, systems and methods, and, in specific embodiments, to systems and methods for aligning and/or connecting medical device system components.

2. Related Art

According to modern medical techniques, certain chronic diseases may be treated by delivering a medication or other substance to the body of a patient. For example, diabetes is a chronic disease that is commonly treated by delivering defined amounts of insulin to a patient at appropriate times. Traditionally, manually operated syringes and insulin pens have been employed for delivering insulin to a patient. More recently, modern systems have been designed to include programmable pumps for delivering controlled amounts of medication to a patient.

Pump type delivery devices have been configured in external devices, which connect to a patient, and have been configured in implantable devices, which are implanted inside of the body of a patient. External pump type delivery devices include devices designed for use in a stationary location, such as a hospital, a clinic, or the like, and further include devices configured for ambulatory or portable use, such as devices designed to be carried by a patient, or the like. External pump-type delivery devices may contain reservoirs of fluidic media, such as, but is not limited to, insulin.

External pump-type delivery devices may be connected in fluid flow communication to a patient or user-patient, for example, through suitable hollow tubing. The hollow tubing may be connected to a hollow needle that is designed to pierce the skin of the patient and to deliver fluidic media there through. Alternatively, the hollow tubing may be connected directly to the patient as through a cannula, or the like.

Examples of some external pump type delivery devices are described in U.S. patent application Ser. No. 11/211,095, filed Aug. 23, 2005, titled "Infusion Device And Method With Disposable Portion" and Published PCT Application WO 01/70307 (PCT/US01/09139) titled "Exchangeable Electronic Cards For Infusion Devices" (each of which is owned by the assignee of the present invention), Published PCT Application WO 04/030716 (PCT/US2003/028769) titled "Components And Methods For Patient Infusion Device," Published PCT Application WO 04/030717 (PCT/US2003/029019) titled "Dispenser Components And Methods For Infusion Device," U.S. Patent Application Publication No. 2005/0065760 titled "Method For Advising Patients Concerning Doses Of Insulin," and U.S. Pat. No. 6,589,229 titled "Wearable Self-Contained Drug Infusion Device," each of which is incorporated herein by reference in its entirety.

External pump-type delivery devices may be connected in fluid-flow communication to a patient-user, for example, through suitable hollow tubing. The hollow tubing may be connected to a hollow needle that is designed to pierce the patient-user's skin and deliver an infusion medium to the patient-user. Alternatively, the hollow tubing may be connected directly to the patient-user as or through a cannula or set of micro-needles.

In contexts in which the hollow tubing is connected to the patient-user through a hollow needle that pierces skin of the user-patient, a manual insertion of the needle into the patient-user can be somewhat traumatic to the user-patient. Accordingly, insertion mechanisms have been made to assist the insertion of a needle into the user-patient, whereby a needle is forced by a spring to move quickly from a retracted position into an extended position. As the needle is moved into the extended position, the needle is quickly forced through the skin of the user-patient in a single, relatively abrupt motion that can be less traumatic to certain user-patients as compared to a slower, manual insertion of a needle. While a quick thrust of the needle into the skin of the user-patient may be less traumatic to some user-patients than a manual insertion, it is believed that, in some contexts, some user-patients may feel less trauma if the needle is moved a very slow, steady pace.

Examples of insertion mechanisms that may be used with and may be built into a delivery device are described in: U.S. patent application Ser. No. 11/645,435, filed Dec. 26, 2006, titled "Infusion Medium Delivery system, Device And Method With Needle Inserter And Needle Inserter Device And Method,"; and U.S. patent application Ser. No. 11/211,095, filed Aug. 23, 2005, titled "Infusion Device And Method With Disposable Portion" (each of which is assigned to the assignee of the present invention), each of which is incorporated herein by reference in its entirety. Other examples of insertion tools are described in U.S. Patent Application Publication No. 2002/0022855, titled "Insertion Device For An Insertion Set And Method Of Using The Same" (assigned to the assignee of the present invention), which is incorporated herein by reference in its entirety. Other examples of needle/cannula insertion tools that may be used (or modified for use) to insert a needle and/or cannula, are described in, for example U.S. patent application Ser. No. 10/389,132 filed Mar. 14, 2003, and entitled "Auto Insertion Device For Silhouette Or Similar Products," and/or U.S. patent application Ser. No. 10/314,653 filed Dec. 9, 2002, and entitled "Insertion Device For Insertion Set and Method of Using the Same," both of which are incorporated herein by reference in their entirety.

Pump-type delivery devices can allow accurate doses of insulin to be calculated and delivered automatically to a patient-user at any time during the day or night. Furthermore, when used in conjunction with glucose sensors or monitors, insulin pumps may be automatically controlled to provide appropriate doses of infusion medium at appropriate times of need, based on sensed or monitored levels of blood glucose.

Pump-type delivery devices have become an important aspect of modern medical treatments of various types of medical conditions, such as diabetes. As pump technologies improve and as doctors and patient-users become more familiar with such devices, the popularity of external medical infusion pump treatment increases and is expected to increase substantially over the next decade.

SUMMARY OF THE DISCLOSURE

A connecting structure for connecting a first member in fluid flow connection with a second member may include, but is not limited to a receptacle structure, a needle, a pierceable member, a connection portion, and a septum. The receptacle structure may be provided on the first member and having an interior chamber and an opening into the interior chamber. The needle may be supported within the interior chamber of the receptacle structure, the needle having a piercing end. The pierceable member may be provided within the interior chamber, adjacent the opening of the receptacle structuring. The pierceable member may surround the piercing end of the needle.

The connection portion may be provided on the second member. The connection portion may have an interior chamber and an opening into the interior chamber of the connection portion. The connection portion may have a size and shape suitable to be received at least partially into the opening of the receptacle structure as the first member and the second member are moved relative to each other. The septum may be supported by the connection portion of the second member in a position to cover the opening of the connection portion. Upon moving the first member and the second member together, the connection portion may be received into the opening of the receptacle structure to push the pierceable member toward the piercing end of the needle to cause the piercing end of the needle to pierce the pierceable member and the septum to come into fluid flow communication with the interior chamber of the connection portion.

In various embodiments, the pierceable member may be collapsible from a first state to a second state. The pierceable member may be collapsed from the first state to the second state as the connection portion pushes the pierceable member toward the end of the needle. In several embodiments, the pierceable member may be expandable from the second state to the first state. The pierceable member may be expanded from the second state to the first state as the connection portion is withdrawn from the opening of the receptacle structure. In several embodiments, the pierceable member may include a plurality of corrugations to allow the pierceable member to be collapsible.

In various embodiments, the pierceable member may have an interior volume. The piercing end of the needle may be arranged in the interior volume of the pierceable member. In various embodiments, the system may include a receptacle supported by the connection portion of the second member in a position to guide the needle as the needle pierces the septum. In several embodiments, the septum may have a first surface and a second surface opposite the first surface. The septum may be positioned in the opening of the connection portion such that the first surface of the septum is pierced by the needle before the second surface of the septum as the first and second members are moved together. The receptacle may be positioned adjacent the first surface of the septum. In several embodiments, wherein the receptacle may be a conically-shaped member.

In various embodiments, the septum may include a perforation through which the piercing end of the needle is inserted. In various embodiments, the second member may include a reservoir for containing fluidic media. The connection portion of the second member may include a portion of the reservoir. In various embodiments, the receptacle structure may be fixed with respect to a base portion. The connection portion of the second member may be provided in a housing that is connectable to the base portion. In various embodiments, the needle may have a first opening into which fluid may flow and a second opening out of which fluid may flow. The second opening of the needle may be provided in fluid flow communication with a needle injection site channel. The needle injection site channel may have an opening that is connectable to a needle inserting device for receiving at least a portion of a needle from the needle inserting device. In several embodiments, the receptacle structure may be fixed with respect to a base portion. The connection portion of the second member may be provided in a housing that is connectable to the base portion. The housing may include a recess through which a needle inserting device may extend when connected to the opening of the needle injection site channel.

In various embodiments, the system may further include a groove and a protrusion. The groove may be provided in one of the receptacle structure and the connection portion. The protrusion may be arranged on the other of the receptacle structure and the connection to be received in the groove of the one of the receptacle structure and the connection portion as the first member and the second member are moved together. Upon moving the first member and the second member together, the protrusion may be received into the groove and the connection portion is received into the opening of the receptacle structure to cause the piercing end of the needle to pierce the septum to come into fluid flow communication with the interior chamber of the connection portion. In several embodiments, the protrusion may be arranged on the connection portion. The needle may be arranged to extend out of the receptacle structure a first distance. The protrusion may include a portion that extends from the connection portion a second distance greater than the first distance that the needle extends out of the receptacle structure. In further embodiments, the protrusion may extend in a same direction as the needle to engage the receptacle before the needle contacts the septum.

In various embodiments, the structure may further include a receptacle and a protrusion member. The receptacle may be provided on a third member. The receptacle may have an interior and an opening into the interior. The protrusion member may be provided on the second member. The protrusion member may have a size and shape suitable to be received at least partially in the opening of the receptacle of the third member. Upon moving the first member and the second member together, the protrusion member may be received into the receptacle and the connection portion is received into the opening of the receptacle structure to cause the piercing end of the needle to pierce the septum to come into fluid flow communication with the interior chamber of the connection portion.

A method of making a connecting structure for connecting a first member in fluid flow connection with a second member may include, but is not limited to, any one or combination of (i) providing a receptacle structure on the first member and having an interior chamber and an opening into the interior chamber; (ii) supporting a needle within the interior chamber of the receptacle structure, the needle having a piercing end; (iii) providing a pierceable member within the interior chamber, adjacent the opening of the receptacle structuring, the pierceable member surrounding the piercing end of the needle; providing a connection portion on the second member, the connection portion having an interior chamber and an opening into the interior chamber of the connection portion, the connection portion having a size and shape suitable to be received at least partially into the opening of the receptacle structure as the first member and the second member are moved relative to each other; and (iv) supporting a septum by the connection portion of the second member in a position to cover the opening of the connection portion;

wherein, upon moving the first member and the second member together, the connection portion is received into the opening of the receptacle structure to push the pierceable member toward the piercing end of the needle to cause the piercing end of the needle to pierce the pierceable member and the septum to come into fluid flow communication with the interior chamber of the connection portion.

An alignment system for aligning a first member in fluid flow connection with a second member may include, but is not limited to, a receptacle structure, a connection portion, a groove, a protrusion, a needle, and a septum. The receptacle structure may be provided on the first member and having an interior chamber and an opening into the interior chamber. The connection portion may be provided on the second member. The connection portion may have an interior chamber and an opening into the interior chamber of the connection portion. The connection portion may have a size and shape suitable to be received at least partially into the opening of the receptacle structure as the first member and the second member are moved relative to each other. The groove provided in one of the receptacle structure and the connection portion.

The protrusion may be arranged on the other of the receptacle structure and the connection portion to be insertable into the groove of the one of the receptacle structure and the connection portion as the opening of the receptacle structure receives the connection portion. The needle may be supported within the interior chamber of the receptacle structure. The needle may have a piercing end. The septum may be supported by the connection portion of the second member in a position to cover the opening of the connection portion. Upon moving the first member and the second member together, the protrusion may be received into the groove and the connection portion is received into the opening of the receptacle structure piercing to cause the piercing end of the needle to pierce the septum to come into fluid flow communication with the interior chamber of the connection portion.

In various embodiments, the protrusion may be arranged on the connection portion. The needle may be arranged to extend out of the receptacle structure a first distance. The protrusion may include a portion that extends from the connection portion a second distance greater than the first distance that the needle extends out of the receptacle structure.

In several embodiments, the protrusion may be arranged on the connection portion such that the portion of the protrusion is received in the groove of the receptacle structure before the needle pierces septum. In several embodiments, the system may further include: a pierceable member provided within the interior chamber, adjacent the opening of the receptacle structuring. The pierceable member may surround the end of the needle. The pierceable member may be arranged to extend out of the receptacle structure a third distance. The second distance that the portion of the protrusion extends from the connection portion may be greater than the third distance that the pierceable member extends out of the receptacle structure. The protrusion may be arranged on the connection portion such that the portion of the protrusion is insertable into the groove of the receptacle structure before the connection portion receives a portion of the pierceable member.

In various embodiments, the protrusion may extend in a same direction as the needle to engage the receptacle before the needle contacts the septum.

In various embodiments, the second member may include a reservoir for containing fluidic media. The connection portion of the second member may include a portion of the reservoir. In several embodiments, the protrusion may extend substantially along the portion of the reservoir.

In various embodiments, the receptacle structure may be fixed with respect to a base portion. The connection portion of the second member may be provided in a housing that is connectable to the base portion. In various embodiments, the structure may further include a receptacle and a protrusion member. The receptacle may be provided on a third member. The receptacle may have an interior and an opening into the interior. The protrusion member may be provided on the second member. The protrusion member may have a size and shape suitable to be received at least partially in the opening of the receptacle of the third member. Upon moving the first member and the second member together, the protrusion member is received into the receptacle and the connection portion is received into the opening of the receptacle structure to cause the piercing end of the needle to pierce the septum to come into fluid flow communication with the interior chamber of the connection portion.

A method of manufacturing an alignment system for aligning a first member in fluid flow connection with a second member may include, but is not limited to, any one of or a combination of (i) providing a receptacle structure on the first member and having an interior chamber and an opening into the interior chamber; (ii) providing a connection portion on the second member, the connection portion having an interior chamber and an opening into the interior chamber of the connection portion, the connection portion having a size and shape suitable to be received at least partially into the opening of the receptacle structure as the first member and the second member are moved relative to each other; providing a groove in one of the receptacle structure and the connection portion; (iii) arranging a protrusion on the other of the receptacle structure and the connection portion to be insertable into the groove of the one of the receptacle structure and the connection portion as the opening of the receptacle structure receives the connection portion; (iv) supporting a needle within the interior chamber of the receptacle structure, the needle having a piercing end; and (v) supporting a septum by the connection portion of the second member in a position to cover the opening of the connection portion; wherein, upon moving the first member and the second member together, the protrusion is received into the groove and the connection portion is received into the opening of the receptacle structure piercing to cause the piercing end of the needle to pierce the septum to come into fluid flow communication with the interior chamber of the connection portion.

An alignment system for aligning a first member in fluid flow connection with a second member may include, but is not limited to, a receptacle structure, a connection portion, a receptacle, and a protrusion member. The receptacle structure may be provided on the first member and having an interior chamber and an opening into the interior chamber. The connection portion may be provided on the second member. The connection portion may have an interior chamber and an opening into the interior chamber of the connection portion. The connection portion may have a size and shape suitable to be received at least partially in the opening of the receptacle structure as the first member and the second member are moved relative to each other.

The receptacle may be provided on a third member, the receptacle having an interior and an opening into the interior. The protrusion member may be provided on the second member. The protrusion member may have a size and shape suitable to be received at least partially in the opening of the receptacle of the third member. Upon moving the first member and the second member together, the protrusion member is received into the receptacle and the connection portion is received into the opening of the receptacle structure piercing to cause the piercing end of the needle to pierce the septum to come into fluid flow communication with the interior chamber of the connection portion.

In various embodiments, the second member may include a reservoir for containing fluidic media. The connection portion of the second member may include a portion of the reservoir. In several embodiments, the protrusion member may be separate and apart from the portion of the reservoir. In several embodiments, the portion of the reservoir may include a port of the reservoir from which fluidic media is expelled.

In various embodiments, the receptacle structure may be fixed with respect to a base portion. The connection portion of the second member may be provided in a housing that is connectable to the base portion. In various embodiments, the second opening of the needle may be provided in fluid flow communication with a needle injection site channel. The needle injection site channel may have an opening that is connectable to a needle inserting device for receiving at least a portion of a needle from the needle inserting device.

In various embodiments, the receptacle structure may be fixed with respect to a base portion. The connection portion of the second member may be provided in a housing that is connectable to the base portion. The housing may include a recess through which a needle inserting device may extend when connected to the opening of the needle injection site channel.

In various embodiments, the system may further include a needle and a septum. The needle may be supported within the interior chamber of the receptacle structure, the needle having a piercing end. The septum may be supported by the connection portion of the second member in a position to cover the opening of the connection portion. Upon moving the first member and the second member together, the protrusion is received into the groove and the connection portion is received into the opening of the receptacle structure to cause the piercing end of the needle to pierce the septum to come into fluid flow communication with the interior chamber of the connection portion.

In several embodiments, the protrusion member may extend in a same direction as the needle to engage the receptacle before the needle contacts the septum.

In several embodiments, the system may further include a pierceable member provided within the interior chamber, adjacent the opening of the receptacle structuring. The pierceable member may surround the end of the needle. The pierceable member may be arranged to extend out of the receptacle structure a third distance. The second distance that the portion of the protrusion extends from the connection portion may be greater than the third distance that the pierceable member extends out of the receptacle structure. The protrusion may be arranged on the connection portion such that the portion of the protrusion is insertable into the groove of the receptacle structure before the connection portion receives a portion of the pierceable member.

A method of manufacturing an alignment system for aligning a first member in fluid flow connection with a second member may include, but is not limited to, any one or combination of (i) providing a receptacle structure on the first member and having an interior chamber and an opening into the interior chamber; (ii) providing a connection portion on the second member, the connection portion having an interior chamber and an opening into the interior chamber of the connection portion, the connection portion having a size and shape suitable to be received at least partially in the opening of the receptacle structure as the first member and the second member are moved relative to each other; providing a receptacle on a third member, the receptacle having an interior and an opening into the interior; and (iii) providing a protrusion member on the second member, the protrusion member having a size and shape suitable to be received at least partially in the opening of the receptacle of the third member; wherein, upon moving the first member and the second member together, the protrusion member is received into the receptacle and the connection portion is received into the opening of the receptacle structure piercing to cause the piercing end of the needle to pierce the septum to come into fluid flow communication with the interior chamber of the connection portion.

BRIEF DESCRIPTION OF THE DRAWINGS

FIG. 9 illustrates a medical device in accordance with an embodiment of the present invention;

FIG. 10 illustrates a medical device in accordance with an embodiment of the present invention;

DETAILED DESCRIPTION

Figure 1:
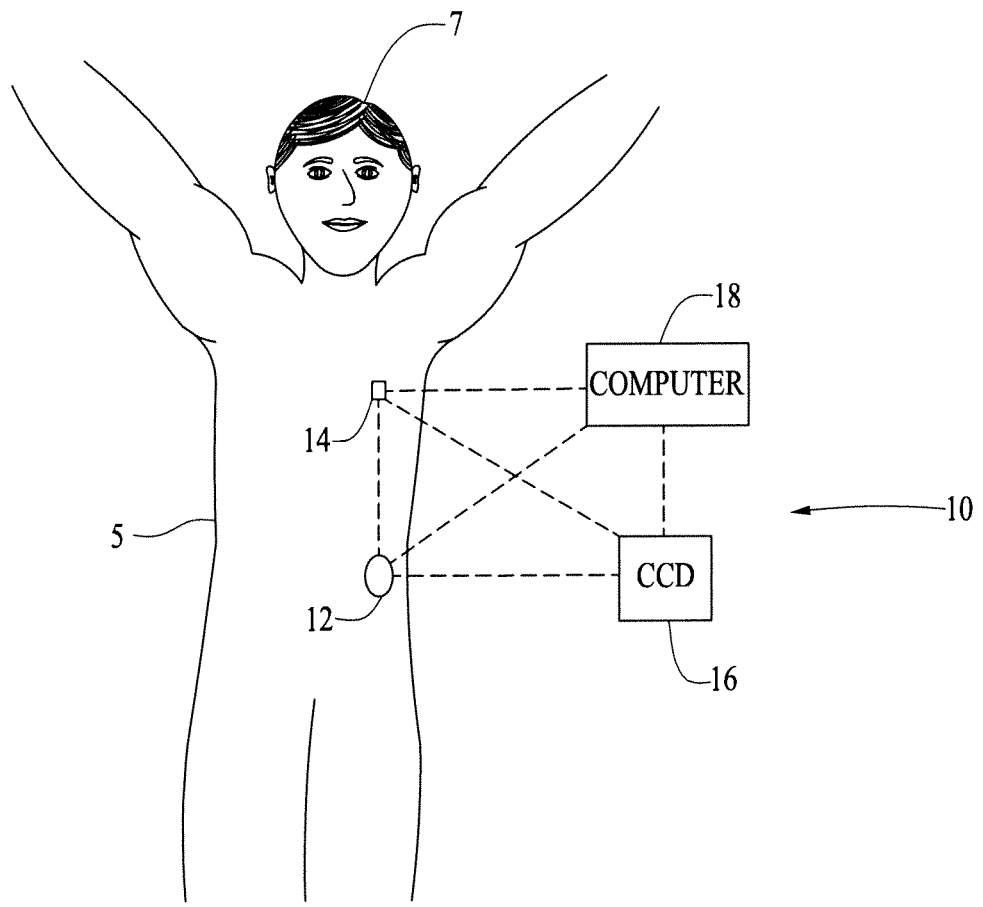
FIG. 1 illustrates a generalized representation of a system in accordance with an embodiment of the present invention.

FIG. 1 illustrates a generalized representation of a system 10 in accordance with an embodiment of the present invention. The system 10 may include a delivery device 12. The system 10 may further include a sensing device 14, a command control device (CCD) 16, and a computer 18. In various embodiments, the delivery device 12 and the sensing device 14 may be secured at desired locations on the body 5 of a patient or user-patient 7. The locations at which the delivery device 12 and the sensing device 14 are secured to the body 5 of the user-patient 7 in FIG. 1 are provided only as representative, non-limiting, examples. It should be noted user-patient as used throughout the disclosure may include patient-user, patient, or user (e.g., a patient, a medical professional, or other treating the patient).

The system 10, the delivery device 12, the sensing device 14, the CCD 16, and/or computer 18 may be similar to (but not limited to) those described in the following U.S. patent applications that were assigned to the assignee of the present invention, where each of following patent applications is incorporated herein by reference in its entirety: (i) U.S. patent application Ser. No. 11/211,095, filed Aug. 23, 2005, "Infusion Device And Method With Disposable Portion"; (ii) U.S. patent application Ser. No. 11/515,225, filed Sep. 1, 2006, "Infusion Medium Delivery Device And Method With Drive Device For Driving Plunger In Reservoir"; (iii) U.S. patent application Ser. No. 11/588,875, filed Oct. 27, 2006, "Systems And Methods Allowing For Reservoir Filling And Infusion Medium Delivery"; (iv) U.S. patent application Ser. No. 11/588,832, filed Oct. 27, 2006, "Infusion Medium Delivery Device And Method With Drive Device For Driving Plunger In Reservoir"; (v) U.S. patent application Ser. No. 11/588,847, filed Oct. 27, 2006, "Infusion Medium Delivery Device And Method With Compressible Or Curved Reservoir Or Conduit"; (vi) U.S. patent application Ser. No. 11/589,323, filed Oct. 27, 2006, "Infusion Pumps And Methods And Delivery Devices And Methods With Same"; (vii) U.S. patent application Ser. No. 11/602,173, filed Nov. 20, 2006, "Systems And Methods Allowing For Reservoir Filling And Infusion Medium Delivery"; (viii) U.S. patent application Ser. No. 11/602,052, filed Nov. 20, 2006, "Systems And Methods Allowing For Reservoir Filling And Infusion Medium Delivery"; (ix) U.S. patent application Ser. No. 11/602,428, filed Nov. 20, 2006, "Systems And Methods Allowing For Reservoir Filling And Infusion Medium Delivery"; (x) U.S. patent application Ser. No. 11/602,113, filed Nov. 20, 2006, "Systems And Methods Allowing For Reservoir Filling And Infusion Medium Delivery"; (xi) U.S. patent application Ser. No. 11/604,171, filed Nov. 22, 2006, "Infusion Medium Delivery Device And Method With Drive Device For Driving Plunger In Reservoir"; (xii) U.S. patent application Ser. No. 11/604,172, filed Nov. 22, 2006, "Infusion Medium Delivery Device And Method With Drive Device For Driving Plunger In Reservoir"; (xiii) U.S. patent application Ser. No. 11/606,703, filed Nov. 30, 2006, "Infusion Pumps And Methods And Delivery Devices And Methods With Same"; (xiv) U.S. patent application Ser. No. 11/606,836, filed Nov. 30, 2006, "Infusion Pumps And Methods And Delivery Devices And Methods With Same"; U.S. patent application Ser. No. 11/636,384, filed Dec. 8, 2006, "Infusion Medium Delivery Device And Method With Compressible Or Curved Reservoir Or Conduit"; (xv) U.S. patent application Ser. No. 11/645,993, filed Dec. 26, 2006, "Infusion Medium Delivery Device And Method With Compressible Or Curved Reservoir Or Conduit"; U.S. patent application Ser. No. 11/645,972, filed Dec. 26, 2006, "Infusion Medium Delivery System, Device And Method With Needle Inserter And Needle Inserter Device And Method"; (xvi) U.S. patent application Ser. No. 11/646,052, filed Dec. 26, 2006, "Infusion Medium Delivery System, Device And Method With Needle Inserter And Needle Inserter Device And Method"; (xvii) U.S. patent application Ser. No. 11/645,435, filed Dec. 26, 2006, "Infusion Medium Delivery System, Device And Method With Needle Inserter And Needle Inserter Device And Method"; (xviii) U.S. patent application Ser. No. 11/646,000, filed Dec. 26, 2006, "Infusion Medium Delivery System, Device And Method With Needle Inserter And Needle Inserter Device And Method"; and (xix) U.S. patent application Ser. No. 11/759,725, filed Jun. 7, 2007, "Infusion Medium Delivery Device And Method With Drive Device For Driving Plunger In Reservoir"; (xx) U.S. patent application Ser. No. 11/606,837, filed Nov. 30, 2006, "Method And Apparatus For Enhancing The Integrity Of An Implantable Sensor Device"; (xxi) U.S. patent application Ser. No. 11/702,713, filed Feb. 5, 2007, "Selective Potting For Controlled Failure And Electronic Devices Employing The Same"; (xxii) U.S. patent application Ser. No. 11/843,601, filed Aug. 22, 2007, "System And Method For Sensor Recalibration"; (xxiii) U.S. patent application Ser. No. 11/868,898, filed Oct. 8, 2007, "Multilayer Substrate"; (xxiv) U.S. patent application Ser. No. 11/964,649, filed Dec. 26, 2007, "System And Methods Allowing For Reservoir Air Bubble Management"; (xxv) U.S. patent application Ser. No. 12/111,751, filed Apr. 29, 2008, "Systems And Methods For Reservoir Filling"; (xxvi) U.S. patent application Ser. No. 12/111,815, filed Apr. 29, 2008, "Systems And Methods For Reservoir Air Bubble Management"; (xxvii) U.S. patent application Ser. No. 11/924,402, filed Oct. 25, 2007, "Sensor Substrate And Method Of Fabricating Same"; (xxviii) U.S. patent application Ser. No. 11/929,428, filed Oct. 30, 2007, "Telemetry System And Method With Variable Parameters"; (xxix) U.S. patent application Ser. No. 11/965,578, filed Dec. 27, 2007, "Reservoir Pressure Equalization Systems And Methods"; (xxx) U.S. patent application Ser. No. 12/107,580, filed Apr. 22, 2008, "Automative Filling Systems And Methods"; (xxxi) U.S. patent application Ser. No. 11/964,663, filed Dec. 26, 2007, "Medical Device With Full Options And Selective Enablement/Disablement"; (xxxii) U.S. patent application Ser. No. 10/180,732, filed Jun. 26, 2002, "Communication Station And Software For Interfacing With An Infusion Pump, Analyte Monitor, Analyte Meter, And/or the like"; (xxxiii) U.S. patent application Ser. No. 12/099,738, filed Apr. 8, 2008, "Systems And Methods Allowing For Reservoir Air Bubble Management"; (xxxiv) U.S. patent application Ser. No. 12/027,963, filed Feb. 7, 2008, "Adhesive Patch Systems And Methods"; (xxxv) U.S. patent application Ser. No. 12/121,647, filed May 15, 2008, "Multi-Lumen Catheter"; (xxxvi) U.S. Patent Provisional App. Ser. No. 61/044,269, filed Apr. 11, 2008, "Reservoir Plunger Head Systems And Methods"; (xxxvii) U.S. Patent App. Ser. No. 61/044,292, filed Apr. 11, 2008, "Reservoir Barrier Layer Systems And Methods"; (xxxviii) U.S. Patent Provisional App. Ser. No. 61/044,322, filed Apr. 11, 2008, "Reservoir Seal Retainer Systems And Methods"; (xxxix) U.S. patent application Ser. No. 12/179,502, filed Jul. 24, 2008, "Method For Formulating And Immobilizing A Matrix Protein And A Matrix Protein For Use In A Sensor"; (xl) U.S. patent application Ser. No. 12/336,367, filed Dec. 16, 2008, "Needle Insertions Systems And Methods"; (xli) U.S. patent application Ser. No. 12/166,210, filed Jul. 1, 2008, "Electronic Device For Controlled Failure"; (xlii) U.S. patent application Ser. No. 12/271,134, filed Nov. 14, 2008, "Multilayer Circuit Devices And Manufacturing Methods Using Electroplated Sacrificial Structures"; (xliii) U.S. patent application Ser. No. 12/171,971, filed Jul. 11, 2008, "Infusion Medium Delivery System, Device And Method With Needle Inserter And Needle Inserter Device And Method"; (xliv) U.S. patent application Ser. No. 12/189, 077, filed Aug. 8, 2008, "Packaging System"; (xlv) U.S. patent application Ser. No. 12/179,536, filed Jul. 24, 2008, "Real Time Self-Adjusting Calibration Algorithm"; (xlvii) U.S. patent application Ser. No. 12/277,186, filed Nov. 24, 2008, "Infusion Medium Delivery System, Device And Method With Needle Inserter And Needle Inserter Device And Method"; (xlviii) U.S. patent application Ser. No. 12/211,783, filed Sep. 16, 2008, "Implantable Sensor Method And System"; (xlix) U.S. patent application Ser. No. 12/247,945, filed Oct. 8, 2008, "Infusion Medium Delivery Device And Method With Drive Device For Driving Plunger In Reservoir"; (l) U.S. patent application Ser. No. 12/360,077, filed Jan. 26, 2009, "Reservoir Barrier Layer Systems And Methods"; (li) U.S. patent application Ser. No. 12/345,362, filed Dec. 29, 2008, "Reservoir Seal Retainer Systems And Methods"; (lii) U.S. patent application Ser. No. 12/353,181, filed Jan. 13, 2009, "Systems And Methods Allowing For Reservoir Filling And Infusion Medium Delivery"; (liii) U.S. patent application Ser. No. 12/360,813, filed Jan. 27, 2009, "Multi-Position Infusion Set Device And Process"; (liv) U.S. patent application Ser. No. 12/360,077, filed Jan. 26, 2009, "Reservoir Barrier Layer Systems And Methods"; (lv) U.S. patent application Ser. No. 12/417,976, filed Apr. 3, 2009, "Reservoir Plunger Head Systems And Methods"; (lvi) U.S. patent application Ser. No. 12/553,038, filed Sep. 2, 2009, "Insertion Device Systems And Methods"; (lvii) U.S. patent application Ser. No. 12/499,283, filed Jul. 8, 2009, "Reservoir Filling Systems And Methods"; (lviii) U.S. patent application Ser. No. 12/537,579, filed Aug. 7, 2009, "Transfer Guard Systems And Methods"; (lix) U.S. patent application Ser. No. 12/649,619, filed Dec. 30, 2009, "Alignment Systems And Methods"; (lx) Ser. No. 12/650,287, filed Dec. 30, 2009, "Engagement And Sensing Systems And Methods"; (lxi) U.S. patent application Ser. No. 12/650,378, filed Dec. 30, 2009, "Connection And Alignment Systems And Methods"; (lxii) U.S. patent application Ser. No. 12/405,840, filed Mar. 17, 2009, "Sterile Device And Method For Producing Same"; (lxiii) U.S. patent application Ser. No. 12/411,236, filed Mar. 25, 2009, "Adhesive Patch Systems And Methods"; (lxiv) U.S. patent application Ser. No. 12/419,188, filed Apr. 6, 2009, "Implantable Sensor Electrodes and Electronic Circuitry"; (lxv) U.S. patent application Ser. No. 12/411,247, filed Mar. 25, 2009, "Adhesive Patch Systems And Methods"; (lxvi) U.S. patent application Ser. No. 12/649,172, filed Dec. 29, 2009, "Insertion Device Systems And Methods"; (lxvii) U.S. patent application Ser. No. 12/497,345, filed Jul. 2, 2009, "Infusion Medium Delivery Device And Method With Drive Device For Driving Plunger In Reservoir"; (lxviii) U.S. patent application Ser. No. 12/490,006, filed Jun. 23, 2009, "Safety Limits For Closed-Loop Infusion Pump Control"; (lxix) U.S. patent application Ser. No. 12/533,942, filed Jul. 31, 2009, "Reservoir Barrier Layer Systems And Methods"; (lxx) U.S. patent application Ser. No. 12/547,315, filed Aug. 25, 2009, "Reservoir Barrier Layer Systems And Methods," all of which are herein incorporated by reference in their entirety. In other embodiments, the system 10, delivery device 12, sensing device 14, CCD 16, and computer 18 may have other suitable configurations.

The delivery device 12 may be configured to deliver fluidic media to the body 5 of the user-patient 7. In various embodiments, fluidic media may include a liquid, a fluid, a gel, or the like. In some embodiments, fluidic media may include a medicine or a drug for treating a disease or a medical condition. For example, fluidic media may include insulin for treating diabetes, or may include a drug for treating pain, cancer, a pulmonary disorder, HIV, or the like. In some embodiments, fluidic media may include a nutritional supplement, a dye, a tracing medium, a saline medium, a hydration medium, or the like.

The sensing device 14 may include a sensor, a monitor, or the like, for providing sensor data or monitor data. In various embodiments, the sensing device 14 may be configured to sense a condition of the user-patient 7. For example, the sensing device 14 may include electronics and enzymes reactive to a biological condition, such as a blood glucose level, or the like, of the user-patient 7.

In various embodiments, the sensing device 14 may be secured to the body 5 of the user-patient 7 or embedded in the body 5 of the user-patient 7 at a location that is remote from the location at which the delivery device 12 is secured to the body 5 of the user-patient 7. In various other embodiments, the sensing device 14 may be incorporated within the delivery device 12. In other embodiments, the sensing device 14 may be separate and apart from the delivery device, and may be, for example, part of the CCD 16. In such embodiments, the sensing device 14 may be configured to receive a biological sample, analyte, or the like, to measure a condition of the user-patient 7.

In further embodiments, the sensing device 14 and/or the delivery device 12 may utilize a closed-loop system. Examples of sensing devices and/or delivery devices utilizing closed-loop systems may be found at, but are not limited to, the following references: (i) U.S. Pat. No. 6,088,608, entitled "Electrochemical Sensor And Integrity Tests Therefor"; (ii) U.S. Pat. No. 6,119,028, entitled "Implantable Enzyme-Based Monitoring Systems Having Improved Longevity Due To Improved Exterior Surfaces"; (iii) U.S. Pat. No. 6,589,229, entitled "Implantable Enzyme-Based Monitoring Systems Adapted for Long Term Use"; (iv) U.S. Pat. No. 6,740,072, entitled "System And Method For Providing Closed Loop Infusion Formulation Delivery"; (v) U.S. Pat. No. 6,827,702, entitled "Safety Limits For Closed-Loop Infusion Pump Control"; (vi) U.S. Pat. No. 7,323,142, entitled "Sensor Substrate And Method Of Fabricating Same"; (vii) U.S. patent application Ser. No. 09/360,342, filed Jul. 22, 1999, entitled "Substrate Sensor"; and (viii) U.S. Provisional Patent App. Ser. No. 60/318,060, filed Sep. 7, 2001, entitled "Sensing Apparatus and Process", all of which are incorporated herein by reference in their entirety.

In such embodiments, the sensing device 14 may be configured to sense a condition of the user-patient 7, such as, but not limited to, blood glucose level, or the like. The delivery device 12 may be configured to deliver fluidic media in response to the condition sensed by the sensing device 14. In turn, the sensing device 14 may continue to sense a new condition of the user-patient, allowing the delivery device 12 to deliver fluidic media continuously in response to the new condition sensed by the sensing device 14 indefinitely. In some embodiments, the sensing device 14 and/or the delivery device 12 may be configured to utilize the closed-loop system only for a portion of the day, for example only when the user-patient is asleep or awake.

Each of the delivery device 12, the sensing device 14, the CCD 16, and the computer 18 may include transmitter, receiver, or transceiver electronics that allow for communication with other components of the system 10. The sensing device 14 may be configured to transmit sensor data or monitor data to the delivery device 12. The sensing device 14 may also be configured to communicate with the CCD 16. The delivery device 12 may include electronics and software that are configured to analyze sensor data and to deliver fluidic media to the body 5 of the user-patient 7 based on the sensor data and/or preprogrammed delivery routines.

The CCD 16 and the computer 18 may include electronics and other components configured to perform processing, delivery routine storage, and to control the delivery device 12. By including control functions in the CCD 16 and/or the computer 18, the delivery device 12 may be made with more simplified electronics. However, in some embodiments, the delivery device 12 may include all control functions, and may operate without the CCD 16 and the computer 18. In various embodiments, the CCD 16 may be a portable electronic device. In various embodiments, the delivery device 12 and/or the sensing device 14 may be configured to transmit data to the CCD 16 and/or the computer 18 for display or processing of the data by the CCD 16 and/or the computer 18.

In some embodiments, the sensing device 14 may be integrated into the CCD 16. Such embodiments may allow the user-patient to monitor a condition by providing, for example, a sample of his or her blood to the sensing device 14 to assess his or her condition. In some embodiments, the sensing device 14 and the CCD 16 may be for determining glucose levels in the blood and/or body fluids of the user-patient without the use of, or necessity of, a wire or cable connection between the delivery device 12 and the sensing device 14 and/or the CCD 16.

In some embodiments, the CCD 16 may be for providing information to the user-patient that facilitates the user-patient's subsequent use of a drug delivery system. For example, the CCD 16 may provide information to the user-patient to allow the user-patient to determine the rate or dose of medication to be administered into the body of the user-patient. In other embodiments, the CCD 16 may provide information to the delivery device 12 to control the rate or dose of medication administered into the body of the user-patient Examples of the types of communications and/or control capabilities, as well as device feature sets and/or program options may be found in the following references: (i) U.S. patent application Ser. No. 10/445,477, filed May 27, 2003, entitled "External Infusion Device with Remote Programming, Bolus Estimator and/or Vibration Alarm Capabilities"; (ii) U.S. patent application Ser. No. 10/429,385, filed May 5, 2003, entitled "Handheld Personal Data Assistant (PDA) with a Medical Device and Method of Using the Same"; and (iii) U.S. patent application Ser. No. 09/813,660, filed Mar. 21, 2001, entitled "Control Tabs for Infusion Devices and Methods of Using the Same," all of which are incorporated herein by reference in their entirety.

Figure 2:
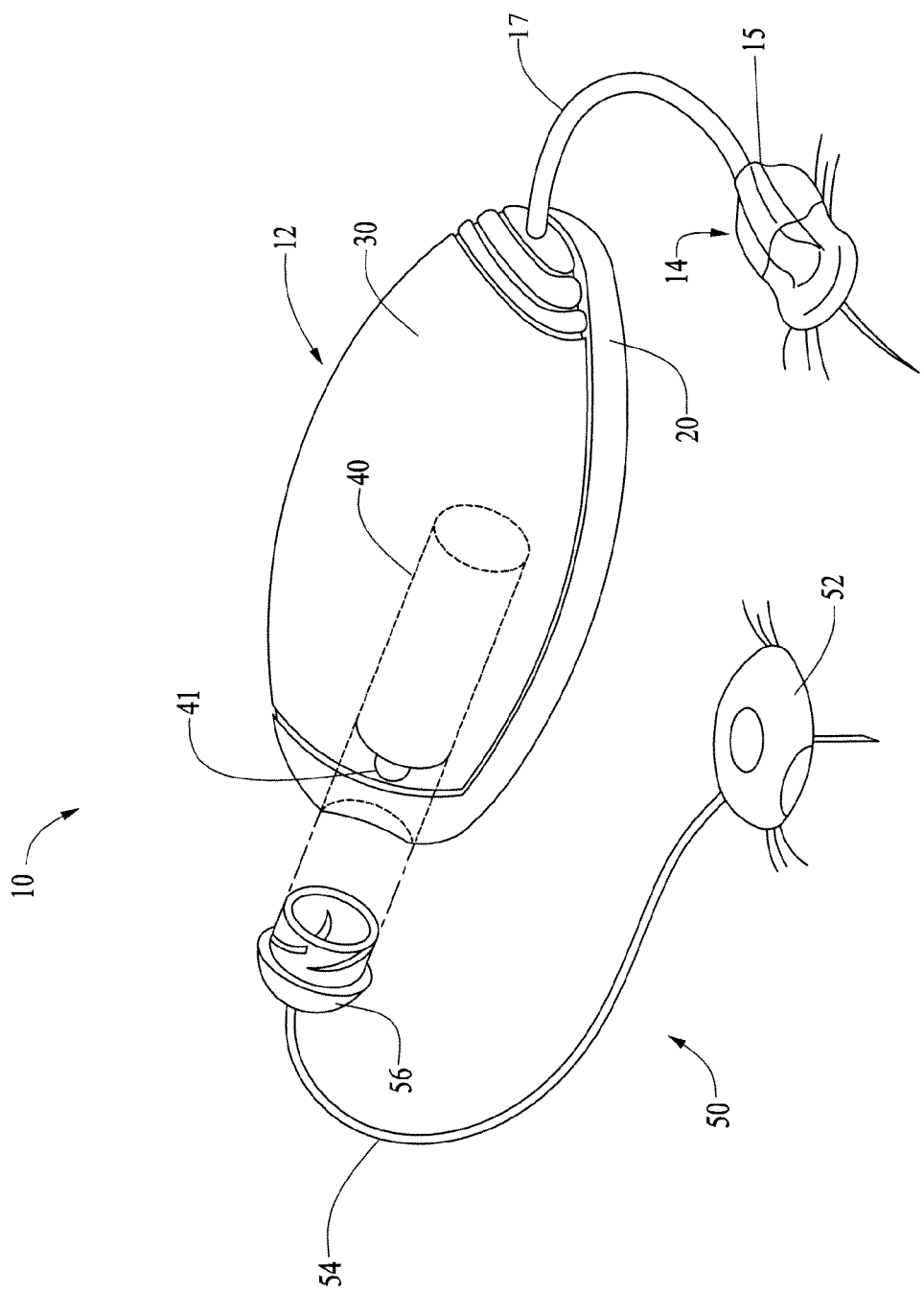
FIG. 2 illustrates an example of a system in accordance with an embodiment of the present invention.

FIG. 2 illustrates an example of the system 10 in accordance with an embodiment of the present invention. The system 10 in accordance with the embodiment illustrated in FIG. 2 includes the delivery device 12 and the sensing device 14. The delivery device 12 in accordance with an embodiment of the present invention may include a disposable housing 20, a durable housing 30, and a reservoir system 40. The delivery device 12 may further include an infusion path 50.

Elements of the delivery device 12 that ordinarily contact the body of a user-patient or that ordinarily contact fluidic media during operation of the delivery device 12 may be considered as a disposable portion of the delivery device 12. For example, a disposable portion of the delivery device 12 may include the disposable housing 20 and the reservoir system 40. The disposable portion of the delivery device 12 may be recommended for disposal after a specified number of uses.

On the other hand, elements of the delivery device 12 that do not ordinarily contact the body of the user-patient or fluidic media during operation of the delivery device 12 may be considered as a durable portion of the delivery device 12. For example, a durable portion of the delivery device 12 may include the durable housing 30, electronics (not shown in FIG. 2), a drive device having a motor and drive linkage (not shown in FIG. 2), and the like. Elements of the durable housing portion of the delivery device 12 are typically not contaminated from contact with the user-patient or fluidic media during normal operation of the delivery device 12 and, thus, may be retained for re-use with replaced disposable portions of the delivery device 12.

In various embodiments, the disposable housing 20 may support the reservoir system 40 and has a bottom surface (facing downward and into the page in FIG. 2) configured to secure to the body of the user-patient. An adhesive may be employed at an interface between the bottom surface of the disposable housing 20 and the skin of the user-patient to adhere the disposable housing 20 to the skin of the user-patient. In various embodiments, the adhesive may be provided on the bottom surface of the disposable housing 20, with a peelable cover layer covering the adhesive material. In this manner, the cover layer may be peeled off to expose the adhesive material, and the adhesive side of the disposable housing 20 may be placed against the user-patient, for example against the skin of the user-patient. Thus in some embodiments, the delivery device 12 may be attached to the skin of the user-patient.

In other embodiments, the disposable housing 20 and/or the remaining portions of the delivery device 12 may be worn or otherwise attached on or underneath clothing of the user-patient. Similarly, the delivery device 12 may be supported by any suitable manner, such as, but not limited to, on a belt, in a pocket, and the like. Representative examples of such delivery devices 12, and delivery devices in general, may include, but is not limited to, the MiniMed Paradigm 522 Insulin Pump, MiniMed Paradigm 722 Insulin Pump, MiniMed Paradigm 515 Insulin Pump, MiniMed Paradigm 715 Insulin Pump, MiniMed Paradigm 512R Insulin Pump, MiniMed Paradigm 712R Insulin Pump, MiniMed 508 Insulin Pump, MiniMed 508R Insulin Pump, and any other derivatives thereof.

The reservoir system 40 may be configured for containing or holding fluidic media, such as, but not limited to insulin. In various embodiments, the reservoir system 40 may include a hollow interior volume for receiving fluidic media, such as, but not limited to, a cylinder-shaped volume, a tubular-shaped volume, or the like. In some embodiments, the reservoir system 40 may be provided as a cartridge or canister for containing fluidic media. In various embodiments, the reservoir system 40 can be refilled with fluidic media. In further embodiments, the reservoir system 40 is pre-filled with fluidic media.

The reservoir system 40 may be supported by the disposable housing 20 in any suitable manner. For example, the disposable housing 20 may be provided with projections or struts (not shown), or a trough feature (not shown), for holding the reservoir system 40. In some embodiments, the reservoir system 40 may be supported by the disposable housing 20 in a manner that allows the reservoir system 40 to be removed from the disposable housing 20 and replaced with another reservoir. Alternatively, or in addition, the reservoir system 40 may be secured to the disposable housing 20 by a suitable adhesive, a strap, or other coupling structure.

In various embodiments, the reservoir system 40 may include at least one port 41 for allowing fluidic media to flow into and/or flow out of the interior volume of the reservoir system 40. In some embodiments, the infusion path 50 may include a connector 56, a tube 54, and a needle apparatus 52. The connector 56 of the infusion path 50 may be connectable to the port 41 of the reservoir system 40. In various embodiments, the disposable housing 20 may be configured with an opening near the port 41 of the reservoir system 40 for allowing the connector 56 of the infusion path 50 to be selectively connected to and disconnected from the port 41 of the reservoir system 40.

In various embodiments, the port 41 of the reservoir system 40 may be covered with or supports a septum (not shown in FIG. 2), such as a self-sealing septum, or the like. The septum may be configured to prevent fluidic media from flowing out of the reservoir system 40 through the port 41 when the septum is not pierced. In addition, in various embodiments, the connector 56 of the infusion path 50 may include a needle for piercing the septum covering the port 41 of the reservoir system 40 to allow fluidic media to flow out of the interior volume of the reservoir system 40.

Examples of needle/septum connectors can be found in U.S. patent application Ser. No. 10/328,393, filed Dec. 22, 2003, entitled "Reservoir Connector," which is incorporated herein by reference in its entirety. In other alternatives, non-septum connectors such as Luer locks, or the like may be used. In various embodiments, the needle apparatus 52 of the infusion path 50 may include a needle that is able to puncture the skin of the user-patient. In addition, in various embodiments, the tube 54 connects the connector 56 with the needle apparatus 52 and may be hollow, such that the infusion path 50 is able to provide a path to allow for the delivery of fluidic media from the reservoir system 40 to the body of a user-patient.

The durable housing 30 of the delivery device 12 in accordance with various embodiments of the present invention includes a housing shell configured to mate with and secure to the disposable housing 20. The durable housing 30 and the disposable housing 20 may be provided with correspondingly shaped grooves, notches, tabs, or other suitable features that allow the two parts to connect together easily, by manually pressing the two housings together, by twist or threaded connection, in a friction fit connection, in a slidable connection, and/or other suitable manner of connecting the parts that is well known in the mechanical arts.

In various embodiments, the durable housing 30 and the disposable housing 20 may be connected to each other using a twist action. The durable housing 30 and the disposable housing 20 may be configured to be separable from each other when a sufficient force is applied to disconnect the two housings from each other. For example, in some embodiments the disposable housing 20 and the durable housing 30 may be snapped together by friction fitting. In various embodiments, a suitable seal, such as an o-ring seal, may be placed along a peripheral edge of the durable housing 30 and/or the disposable housing 20 to provide a seal against water entering between the durable housing 30 and the disposable housing 20.

The durable housing 30 of the delivery device 12 may support a drive device (not shown in FIG. 2) that may include a motor and a drive device linkage portion. The drive device may be configured to apply a force to fluidic media within the reservoir system 40 to force fluidic media out of the reservoir system 40 and into an infusion path, such as the infusion path 50, for delivery to a user-patient. For example, in some embodiments, an electrically-driven motor 84 (refer to FIGS. 5B and 5C) may be mounted within the durable housing 30 with appropriate linkage for operatively coupling the motor 84 to a plunger arm (refer to FIGS. 6A-6C) connected to a plunger head (refer to FIGS. 6A-6C) arranged within the reservoir system 40. The electrically-driven motor may be configured to drive the plunger head in a direction to force fluidic media out of the port 41 of the reservoir system 40 and to the user-patient.

Also, in some embodiments, the motor 84 may be controllable to reverse direction to move the plunger arm 60 and the plunger head to cause fluid to be drawn into the reservoir system 40 from a patient. The motor 84 may be arranged within the durable housing 30 and the reservoir system 40 may be correspondingly arranged on the disposable housing 20, such that the operable engagement of the motor 84 with the plunger head, through the appropriate linkage, occurs automatically upon the user-patient connecting the durable housing 30 with the disposable housing 20 of the delivery device 12. Further examples of linkage and control structures may be found in, but are not limited to, U.S. patent application Ser. No. 09/813,660, filed Mar. 21, 2001, entitled "Control Tabs for Infusion Devices and Methods of Using the Same"; U.S. Patent Pub. No. 2006/0264894 (Ser. No. 11/211,095), filed Aug. 23, 2005, entitled "Infusion Device and Method with Disposable Portion"; U.S. patent application Ser. No. 11/210,467, filed Aug. 23, 2005, entitled "Infusion Device and Method With Drive In Separable Durable Housing Portion"; U.S. patent application Ser. No. 11/211,150, filed Aug. 23, 2005, entitled "Pump Assembly and Method For Infusion Device"; U.S. patent application Ser. No. 11/210,455, filed Aug. 23, 2005, entitled "Reservoir Support And Method For Infusion Device"; and U.S. Pat. No. 6,485,465, filed Mar. 27, 2001, entitled "Methods, Apparatuses, and Uses for Infusion Pump Fluid Pressure and Force Detection," all of which are incorporated herein by reference in its entirety.

In various embodiments, the durable housing 30 and the disposable housing 20 may be made of suitably rigid materials that maintain their shape, yet provide sufficient flexibility and resilience to effectively connect together and disconnect, as described above. The material of the disposable housing 20 may be selected for suitable compatibility with skin. For example, the disposable housing 20 and the durable housing 30 of the delivery device 12 may be made of any suitable plastic, metal, composite material, or the like. The disposable housing 20 may be made of the same type of material or a different material relative to the durable housing 30. In some embodiments, the disposable housing 20 and the durable housing 30 may be manufactured by injection molding or other molding processes, machining processes, or combinations thereof.

For example, the disposable housing 20 may be made of a relatively flexible material, such as a flexible silicone, plastic, rubber, synthetic rubber, or the like. By forming the disposable housing 20 of a material capable of flexing with the skin of a user-patient, a greater level of user-patient comfort may be achieved when the disposable housing 20 is secured to the skin of the user-patient. In addition, a flexible disposable housing 20 may result in an increase in site options on the body of the user-patient at which the disposable housing 20 may be secured.

In the embodiment illustrated in FIG. 2, the delivery device 12 is connected to the sensing device 14 through a connection element 17 of the sensing device 14. The sensing device 14 may include a sensor 15 that includes any suitable biological or environmental sensing device, depending upon a nature of a treatment to be administered by the delivery device 12. For example, in the context of delivering insulin to a diabetes patient, the sensor 15 may include a blood glucose sensor, or the like.

In some embodiments, the sensor 15 may include a continuous glucose sensor. The continuous glucose sensor may be implantable within the body of the user-patient. In other embodiments, the continuous glucose sensor may be located externally, for example on the skin of the user-patient, or attached to clothing of the user-patient. In such embodiments, fluid may be drawn continually from the user-patient and sensed by the continuous glucose sensor. In various embodiments, the continuous glucose sensor may be configured to sense and/or communicate with the CCD 16 continuously. In other embodiments, the continuous glucose sensor may be configured to sense and/or communicate with the CCD 16 intermittently, for example sense glucose levels and transmit information every few minutes. In various embodiments, the continuous glucose sensor may utilize glucose oxidase.

The sensor 15 may be an external sensor that secures to the skin of a user-patient or, in other embodiments, may be an implantable sensor that is located in an implant site within the body of the user-patient. In further alternatives, the sensor may be included with as a part or along side the infusion cannula and/or needle, such as for example as shown in U.S. patent application Ser. No. 11/149,119, filed Jun. 8, 2005, entitled "Dual Insertion Set," which is incorporated herein by reference in its entirety. In the illustrated example of FIG. 2, the sensor 15 is an external sensor having a disposable needle pad that includes a needle for piercing the skin of the user-patient and enzymes and/or electronics reactive to a biological condition, such as blood glucose level or the like, of the user-patient. In this manner, the delivery device 12 may be provided with sensor data from the sensor 15 secured to the user-patient at a site remote from the location at which the delivery device 12 is secured to the user-patient.

While the embodiment shown in FIG. 2 may include a sensor 15 connected by the connection element 17 for providing sensor data to sensor electronics (not shown in FIG. 2) located within the durable housing 30 of the delivery device 12, other embodiments may employ a sensor 15 located within the delivery device 12. Yet other embodiments may employ a sensor 15 having a transmitter for communicating sensor data by a wireless communication link with receiver electronics (not shown in FIG. 2) located within the durable housing 30 of the delivery device 12. In various embodiments, a wireless connection between the sensor 15 and the receiver electronics within the durable housing 30 of the delivery device 12 may include a radio frequency (RF) connection, an optical connection, or another suitable wireless communication link. Further embodiments need not employ the sensing device 14 and, instead, may provide fluidic media delivery functions without the use of sensor data.

As described above, by separating disposable elements of the delivery device 12 from durable elements, the disposable elements may be arranged on the disposable housing 20, while durable elements may be arranged within a separable durable housing 30. In this regard, after a prescribed number of uses of the delivery device 12, the disposable housing 20 may be separated from the durable housing 30, so that the disposable housing 20 may be disposed of in a proper manner. The durable housing 30 may then be mated with a new (unused) disposable housing 20 for further delivery operation with a user-patient.

Figure 3:
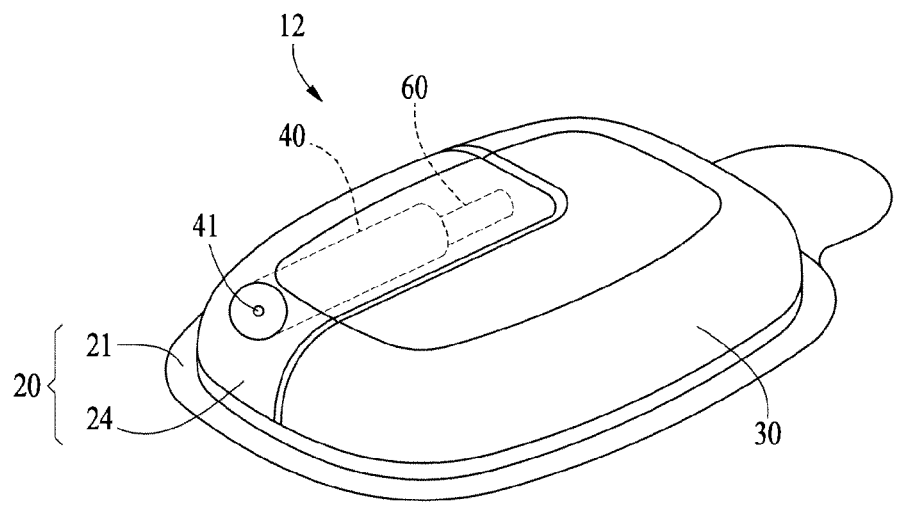
FIG. 3 illustrates an example of a delivery device in accordance with an embodiment of the present invention.

FIG. 3 illustrates an example of the delivery device 12 in accordance with another embodiment of the present invention. The delivery device 12 of the embodiment of FIG. 3 is similar to the delivery device 12 of the embodiment of FIG. 2. While the delivery device 12 in the embodiment illustrated in FIG. 2 provides for the durable housing 30 to cover the reservoir system 40, the delivery device 12 in the embodiment of FIG. 3 provides for the durable housing 30 to secure to the disposable housing 20 without covering the reservoir system 40. The delivery device 12 of the embodiment illustrated in FIG. 3 includes the disposable housing 20, and the disposable housing 20 in accordance with the embodiment illustrated in FIG. 3 includes a base 21 and a reservoir retaining portion 24. In one embodiment, the base 21 and reservoir retaining portion 24 may be formed as a single, unitary structure.

The base 21 of the disposable housing 20 may be configured to be securable to a body of a user-patient. The reservoir-retaining portion 24 of the disposable housing 20 is configured to house the reservoir system 40. The reservoir-retaining portion 24 of the disposable housing 20 may be configured to have an opening to allow for the port 41 of the reservoir system 40 to be accessed from outside of the reservoir-retaining portion 24 while the reservoir system 40 is housed in the reservoir-retaining portion 24. The durable housing 30 may be configured to be attachable to and detachable from the base 21 of the disposable housing 20. The delivery device 12 in the embodiment illustrated in FIG. 3 includes a plunger arm 60 that is connected to or that is connectable to a plunger head (not shown in FIG. 3) within the reservoir system 40.

Figure 4:
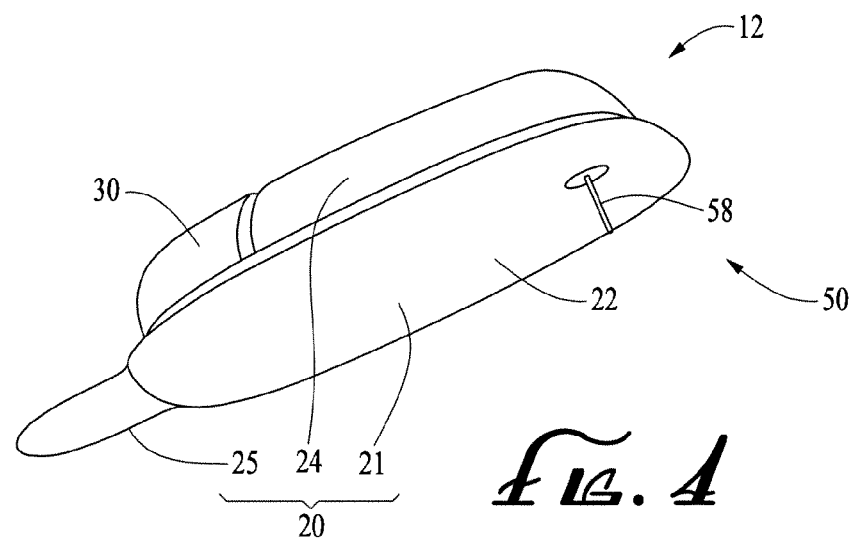
FIG. 4 illustrates a delivery device in accordance with an embodiment of the present invention.

FIG. 4 illustrates another view of the delivery device 12 of the embodiment of FIG. 3. The delivery device 12 of the embodiment illustrated in FIG. 4 includes the disposable housing 20, the durable housing 30, and the infusion path 50. The disposable housing 20 in the embodiment of FIG. 4 includes the base 21, the reservoir-retaining portion 24, and a peelable cover layer 25. The peelable cover layer 25 may cover an adhesive material on the bottom surface 22 of the base 21. The peelable cover layer 25 may be configured to be peelable by a user-patient to expose the adhesive material on the bottom surface 22 of the base 21. In some embodiments, there may be multiple adhesive layers on the bottom surface 22 of the base 21 that are separated by peelable layers.

The infusion path 50 in accordance with the embodiment of the present invention illustrated in FIG. 4 includes the needle 58 rather than the connector 56, the tube 54, and the needle apparatus 52 as shown in the embodiment of FIG. 2. The base 21 of the disposable housing 20 may be provided with an opening or pierceable wall in alignment with a tip of the needle 58, to allow the needle 58 to pass through the base 21 and into the skin of a user-patient under the base 21, when extended. In this manner, the needle 58 may be used to pierce the skin of the user-patient and deliver fluidic media to the user-patient.

Alternatively, the needle 58 may be extended through a hollow cannula (not shown in FIG. 4), such that upon piercing the skin of the user-patient with the needle 58, an end of the hollow cannula is guided through the skin of the user-patient by the needle 58. Thereafter, the needle 58 may be removed, leaving the hollow cannula in place with one end of the cannula located within the body of the user-patient and the other end of the cannula in fluid flow connection with fluidic media within the reservoir system 40. Accordingly, fluidic media may be conveyed from the reservoir system 40 to the body of the user-patient.

Figure 5A:
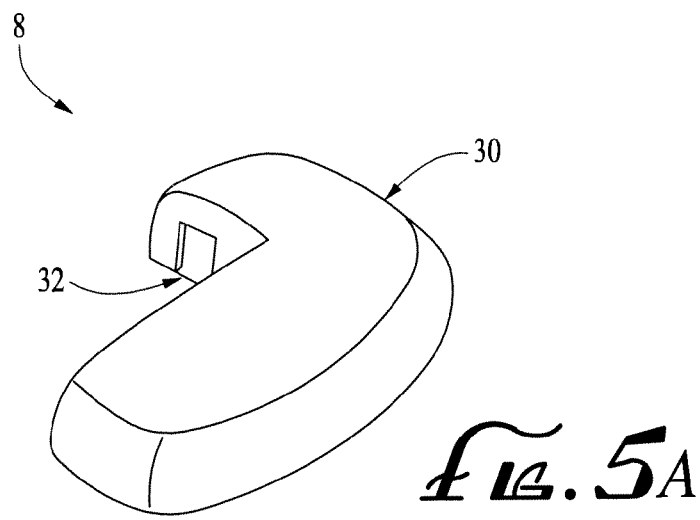
FIG. 5A illustrates a durable portion of a delivery device in accordance with an embodiment of the present invention.
Figure 5B:
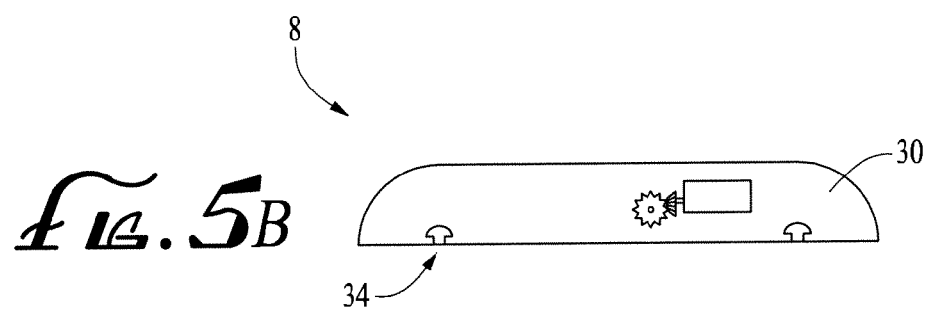
FIG. 5B illustrates a section view of a durable portion of a delivery device in accordance with an embodiment of the present invention.
Figure 5C:
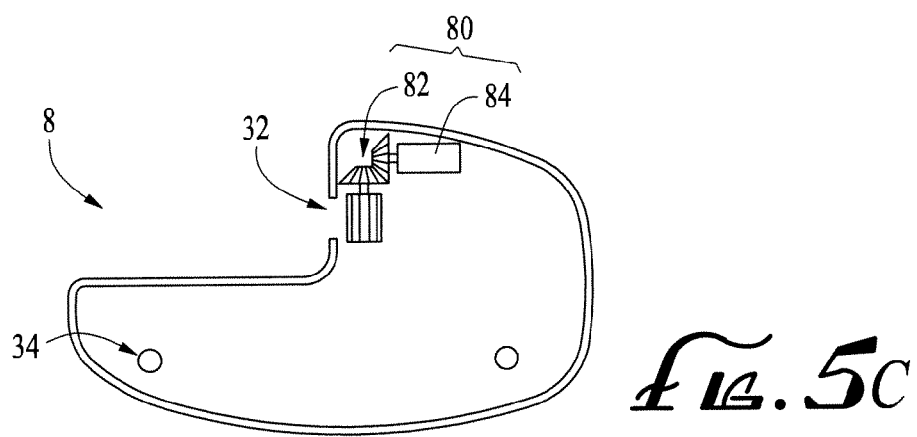
FIG. 5C illustrates a section view of a durable portion of a delivery device in accordance with an embodiment of the present invention.

FIG. 5A illustrates a durable portion 8 of the delivery device 12 (e.g., FIG. 3) in accordance with an embodiment of the present invention. FIG. 5B illustrates a section view of the durable portion 8 in accordance with an embodiment of the present invention. FIG. 5C illustrates another section view of the durable portion 8 in accordance with an embodiment of the present invention. With reference to FIGS. 5A, 5B, and 5C, in various embodiments, the durable portion 8 may include the durable housing 30, and a drive device 80. The drive device 80 may include a motor 84 and a drive device linkage portion 82.

In various embodiments, the durable housing 30 may include an interior volume for housing the motor 84, the drive device linkage portion 82, other electronic circuitry, and a power source (not shown in FIGS. 5A, 5B, and 5C). In addition, in various embodiments, the durable housing 30 may be configured with an opening 32 for receiving a plunger arm 60 (refer to FIG. 3). In addition, in various embodiments, the durable housing 30 may include one or more connection members 34, such as tabs, insertion holes, or the like, for connecting with the base 21 of the disposable housing 20 (e.g., FIG. 3).

Figure 6A:
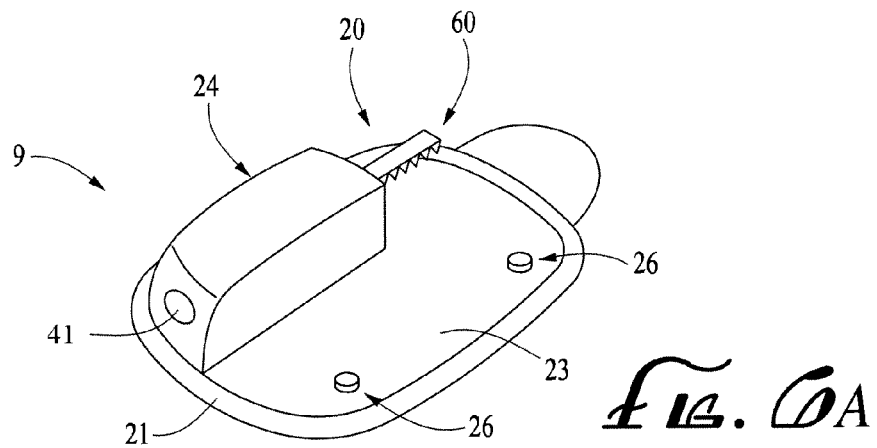
FIG. 6A illustrates a disposable portion of a delivery device in accordance with an embodiment of the present invention.
Figure 6B:
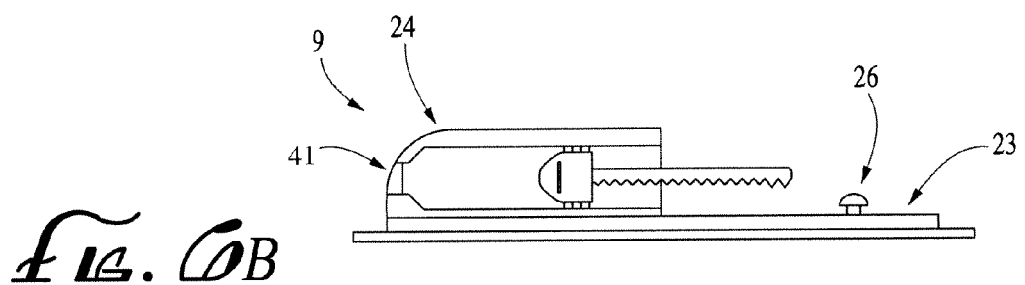
FIG. 6B illustrates a section view of a disposable portion of a delivery device in accordance with an embodiment of the present invention.
Figure 6C:
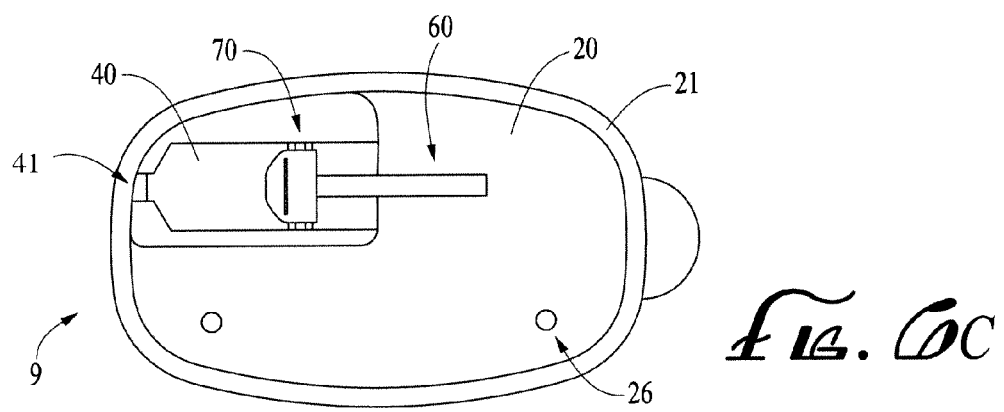
FIG. 6C illustrates a section view of a disposable portion of a delivery device in accordance with an embodiment of the present invention.

FIG. 6A illustrates a disposable portion 9 of the delivery device 12 (e.g., FIG. 3) in accordance with an embodiment of the present invention. FIG. 6B illustrates a section view of the disposable portion 9 in accordance with an embodiment of the present invention. FIG. 6C illustrates another section view of the disposable portion 9 in accordance with an embodiment of the present invention. With reference to FIGS. 6A, 6B, and 6C, in various embodiments, the disposable portion 9 includes the disposable housing 20, the reservoir system 40, the plunger arm 60, and a plunger head 70. The plunger head 70 may be made of Bromobutyl rubber, silicone rubber, or any other suitable material and/or any derivative thereof. In some embodiments, the disposable housing 20 may include the base 21 and the reservoir-retaining portion 24. In various embodiments, the base 21 may include a top surface 23 having one or more connection members 26, such as tabs, grooves, or the like, for allowing connections with the one or more connection members 34 of embodiments of the durable housing 30 (e.g., FIG. 5B).

In various embodiments, the reservoir system 40 may be housed within the reservoir retaining portion 24 of the disposable housing 20, and the reservoir system 40 may be configured to hold fluidic media. In addition, in various embodiments, the plunger head 70 may be disposed at least partially within the reservoir system 40 and may be moveable within the reservoir system 40 to allow fluidic media to fill into the reservoir system 40 and to force fluidic media out of the reservoir system 40. In some embodiments, the plunger arm 60 may be connected to or is connectable to the plunger head 70.

Also, in some embodiments, a portion of the plunger arm 60 may extend to outside of the reservoir-retaining portion 24 of the disposable housing 20. In various embodiments, the plunger arm 60 may have a mating portion for mating with the drive device linkage portion 82 of the drive device 80 (e.g., FIG. 5C). With reference to FIGS. 5C and 6C, in some embodiments, the durable housing 30 may be snap fitted onto the disposable housing 20, whereupon the drive device linkage portion 82 automatically engages the mating portion of the plunger arm 60.

When the durable housing 30 and the disposable housing 20 are fitted together with the drive device linkage portion 82 engaging or mating with the plunger arm 60, the motor 84 may be controlled to drive the drive device linkage portion 82. Accordingly, the plunger arm 60 may be moved to cause the plunger head 70 to move within the reservoir system 40. When the interior volume of the reservoir system 40 is sufficiently filled with fluidic media and an infusion path is provided from the reservoir system 40 to the body of the user-patient, the plunger head 70 may be moved within the reservoir system 40 to force fluidic media from the reservoir system 40 to the user-patient via the infusion path.

In various embodiments, once the reservoir system 40 has been sufficiently emptied or otherwise requires replacement, the user-patient may simply remove the durable housing 30 from the disposable housing 20, and replace the disposable portion 9, including the reservoir system 40, with a new disposable portion having a new reservoir. The durable housing 30 may be connected to the new disposable housing of the new disposable portion, and the delivery device including the new disposable portion may be secured to the skin of a user-patient, or otherwise attached to the user-patient.

In various other embodiments, rather than replacing the entire disposable portion 9 every time the reservoir system 40 is emptied, the reservoir system 40 may be refilled with fluidic media. In some embodiments, the reservoir system 40 may be refilled while remaining within the reservoir retaining portion 24 (e.g., FIG. 6B) of the disposable housing 20. In addition, in various embodiments, the reservoir system 40 may be replaced with a new reservoir (not shown), while the disposable housing 20 may be re-used with the new reservoir. In such embodiments, the new reservoir may be inserted into the disposable portion 9.

With reference to FIGS. 3, 5A, 6B, and 6C, in various embodiments, the delivery device 12 may include reservoir status circuitry (not shown), and the reservoir system 40 may include reservoir circuitry (not shown). In various embodiments, the reservoir circuitry stores information such as, but not limited to, at least one of (i) an identification string identifying the reservoir system 40; (ii) a manufacturer of the reservoir system 40; (iii) contents of the reservoir system 40; (iv) an amount of contents in the reservoir system 40; or the like. In some embodiments, the delivery device 12 may include the reservoir status circuitry, and the reservoir status circuitry may be configured to read data from the reservoir circuitry when the reservoir system 40 is inserted into the disposable portion 9.

In various embodiments, the reservoir status circuitry may be further configured to store data to the reservoir circuitry after at least some of the contents of the reservoir system 40 have been transferred out of the reservoir system 40 to update information in the reservoir circuitry. Such information may be related to, but is not limited to, an amount of fluidic media remaining in the reservoir system 40, an amount of fluidic media already delivered, plunger head 60 location, pressure within the reservoir system, or the like.

In some embodiments, the reservoir status circuitry may be configured to store data to the reservoir circuitry to update information in the reservoir circuitry related to an amount of contents remaining in the reservoir system 40 when the reservoir system 40 is inserted into the disposable portion 9. In some embodiments, the delivery device 12 may include the reservoir status circuitry and the reservoir system 40 may include the reservoir circuitry, and the reservoir status circuitry may selectively inhibit use of the delivery device 12 or may selectively provide a warning signal based on information read by the reservoir status circuitry from the reservoir circuitry.

Various embodiments relate, generally, to needle inserter or inserting devices and methods and medical devices, such as, but not limited to sensors, monitors and infusion medium delivery systems, devices and methods that include such needle-inserting devices and methods. The needle-inserting device and method may operate to insert a needle or cannula through skin of a user-patient, for example, to provide a fluid flow path for conveying an infusion medium through a hollow channel in the needle or cannula and into the user-patient and/or to convey a fluid from the user-patient to one or more sensor elements. Embodiments of the present invention may be configured, as described herein, to provide a reliable, cost effective, and easy-to-use mechanism for inserting a needle or cannula to a specific depth into a user-patient with minimal traumatic effect.

In addition, embodiments may be configured to establish a contiguous fluid flow passage for fluid transfer between a reservoir and the user-patient when the hollow needle or cannula is inserted into the user-patient. Needle-inserting devices according to embodiments of the present invention may be used with, connectable to and disconnectable from, or incorporated in a portion of an infusion medium delivery system. For example, a needle-inserting device may be connectable to a base structure of a pump-type delivery device for insertion of a needle, after which the needle-inserting device may be removed from the base structure, whereupon a further housing portion of the delivery device (containing components such as, but not limited to, a reservoir and pump or drive device) may be coupled to the base structure for operation.

Alternatively, the needle-inserting device may be incorporated into the further housing portion that contains other components as described above. In yet other embodiments, the needle-inserting device may be connectable to (and releasable from) or incorporated within an injection site module or other housing that connects, for example, by flexible tubing, to other components of a medical device (such as, but not limited to an infusion medium delivery device). In yet other embodiments, needle inserter devices may be configured for use with systems other than infusion medium delivery systems, such as, but not limited to sensor and monitor systems, or the like.

The structures and methods described with respect to the embodiments of the disclosure employed in any suitable device or system in which two members that, at some period of time, are not connected in fluid flow communication, are to be connected together in a manner that allows fluid to flow from one member to the other. In one example embodiment, the structure and method is described with respect to a first member including a fluid reservoir for containing an infusion medium that may be connectable to a second member including an injection site structure in which a hollow needle or cannula is or may be inserted into a user-patient, for conveying fluid media to the user-patient. However, a connection structure according to embodiments of the present invention may be employed to connect any two (or more) members together for fluid flow communication with each other.

In FIGS. 7-12, an example of a structure 100 and method for connecting two members in fluid flow communication is described with reference to a first member 102 and a second member 103. The first member 102 may include a housing 104 on a base 106. The housing 104 may be formed integral with the base 106 or may be formed as a separate structure connected to the base 106 in a fixed relation to the base 106. The housing 104 and the base 106 each may be made of any suitably rigid material, including, but not limited to plastic, metal, ceramic, composite material, or the like.

The housing 104 may include an injection site section 105 containing an injection site structure in which a hollow needle or cannula may be inserted into a user-patient for conveying fluidic media to or from the user-patient. The housing 104 may be made of a material of suitable strength and durability such as, but not limited to, plastic, metal, glass, or the like. In other embodiments, instead of or in addition to an injection site, the housing 104 may contain, be part of, or be operatively connected to any other suitable structure for conveying, containing, and/or processing fluidic media.

The second member 103 may also include a housing 108, which in the illustrated embodiment may include a reservoir 107 for containing fluidic media. The reservoir 107 may be configured and/or made of materials as previously described with respect to reservoir system 40 (e.g., FIGS. 1-6C). The second member 103 may be held within or otherwise be covered by an outer housing 109 configured to attach to the base 106. The outer housing 109 may be configured to connect to the base 106 of the first member 102 by any suitable connection structure.

In particular embodiments, at least one of the outer housing 109 and the base 106 may include one or more flexible pawls, protrusions, indentations, or the like for engaging and/or receiving one or more corresponding pawls, protrusions, indentations, or the like on the other of the base 106 and the outer housing 109 to provide a suitable connection structure. Alternatively or in addition, the connection structure may include adhesive material or other suitable connectors.

In other embodiments, the housing 108 may be or be connected to a sensor housing (not shown) containing sensor components. In yet other embodiments, the housing 108 may contain, be part of, or be operatively connected to any other suitable structure for conveying, containing, and/or processing fluidic media. The housing 108 may be made of any suitably rigid material, including, but not limited to, plastic, metal, ceramic, composite material, or the like.

The housing 104 may have or be connected to a receptacle structure 110. The receptacle structure 110 may have an opening 112 leading into a chamber 114 within the receptacle structure 110. In some embodiments, the receptacle structure 110 may be part of the housing 104 adjacent a section of the housing 104 containing the injection site section 105. In other embodiments, the receptacle structure 110 may include a further housing connected to the housing 104.

The receptacle structure 110 may include a first septum 116 located within the chamber 114 and may be moveable within the chamber 114 toward and away from the opening 112. The receptacle structure 110 may also include a bias mechanism 118, which may apply a bias force on the first septum 116 in a direction toward the opening 112. The bias mechanism 118 may be arranged for forcing the first septum 116 against the opening 112. One or more annular protrusions or one or more appropriately shaped or positioned protrusions 120 adjacent the opening 112 may be provided to inhibit the first septum 116 from being forced out of the chamber 114 through the opening 112 by the force of the bias mechanism 118.

The first septum 116 may have a front surface 116a that is at least partially exposed through the opening 112 when the first septum 116 is urged against the opening 112 by the bias mechanism 118. The first septum 116 may have a back surface 116b facing toward an interior of the chamber 114. The first septum 116 may be made of any suitable material that may be pierceable by a needle, such as, but not limited to, a natural or synthetic rubber material, silicon, or the like. In some embodiments, the first septum 116 may be made of a self-sealing material capable of sealing itself after a needle has pierced the first septum 116 and was subsequently withdrawn from the first septum 116.

In some embodiments, the bias mechanism 118 may be a coil spring located within the chamber 114 on an opposite side of the first septum 116 with respect to the front surface 116a. In other embodiments, the bias mechanism 118 may be provided in any suitable manner for biasing the first septum 116 toward the opening 112. These may include, but are not limited to, other types of springs, pressurized fluid within the chamber 114, a collapsible skirt structure extending from the first septum 116 with a natural or built-in spring force, chemical, substance that expands upon contact with another chemical or substance, or upon application of energy from an energy source such as a heat, laser, or other radiation source, or the like. For example, in some embodiments, the first septum 116 may have a flexible accordion-like configuration to allow expansion and contraction of the skirt structure.

A needle 124 may be supported within the chamber 114. The needle 124 may be hollow and may have a sharp end 124a directed toward the back surface 116b of the first septum 116. In some embodiments, the needle 124 may be supported within the bias mechanism 118 such that a longitudinal axial dimension of the needle 124 extends generally parallel to a longitudinal axial dimension of the bias mechanism 118.

The needle 124 may be supported by a supporting structure located within the receptacle structure 110. In some embodiments, the supporting structure may be a wall integral with the receptacle structure 110. The supporting structure may be located, for example, on an opposite end of the chamber 114 relative to the end of the chamber 114 at which the opening 112 is located. In other embodiments, the supporting structure may be any suitable structure that is generally fixed relative to the receptacle structure 110 and is able to support the needle 124 in a generally fixed relation to the receptacle structure 110.

The needle 124 may be made of any suitably rigid material, including, but not limited to metal, plastic, ceramic, or the like, and may have a hollow channel extending in a lengthwise dimension of the needle 124. The hollow channel in the needle 124 may be open on the sharp end 124a of the needle 124 and may be open at another location 124b along the lengthwise dimension of the needle 124, such as, but not limited to, the needle end opposite the sharp end 124a. The hollow channel in the needle 124 may provide a fluid flow path between the sharp end 124a of the needle 124 and the opening 124b of the needle 124. In some embodiments, the opening 124b of the needle 124 may be connected in fluid flow communication with a manifold 128 in the injection site section 105.

The housing 108 of the second member 103 may include a connection portion 130 having a hollow interior chamber 132 and an opening 134 into the interior chamber 132. A second septum 136 may be supported by the housing 108 to seal the opening 134. The second septum 136 may be supported in a fixed relation to the housing 108, for example, within the housing 108 at one end of the interior chamber 132.

Figure 7:
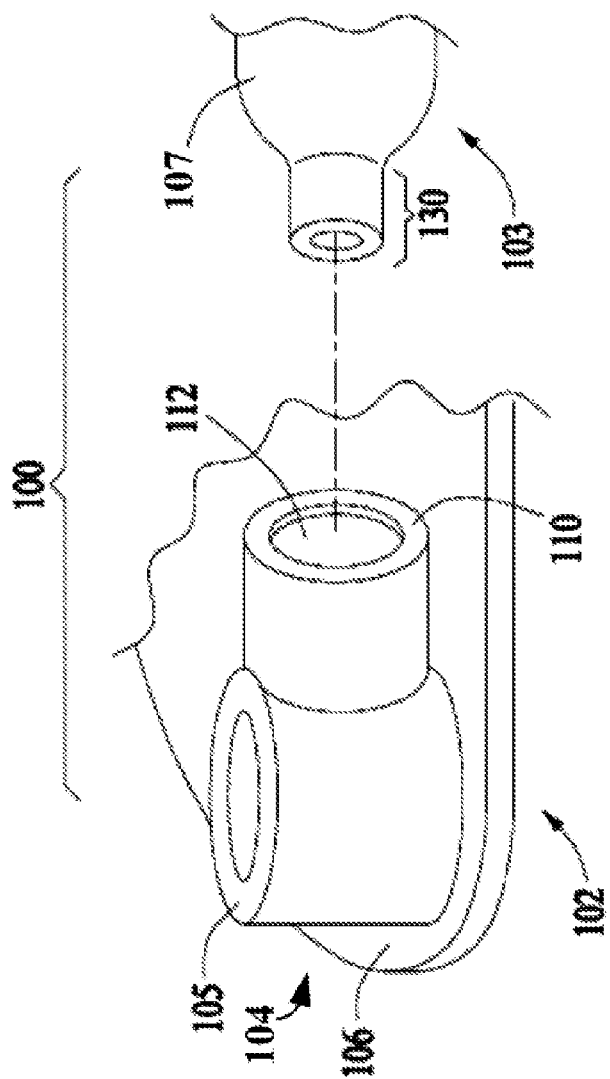
FIG. 7 illustrates portions of a medical device in accordance with an embodiment of the present invention.
Figure 8:
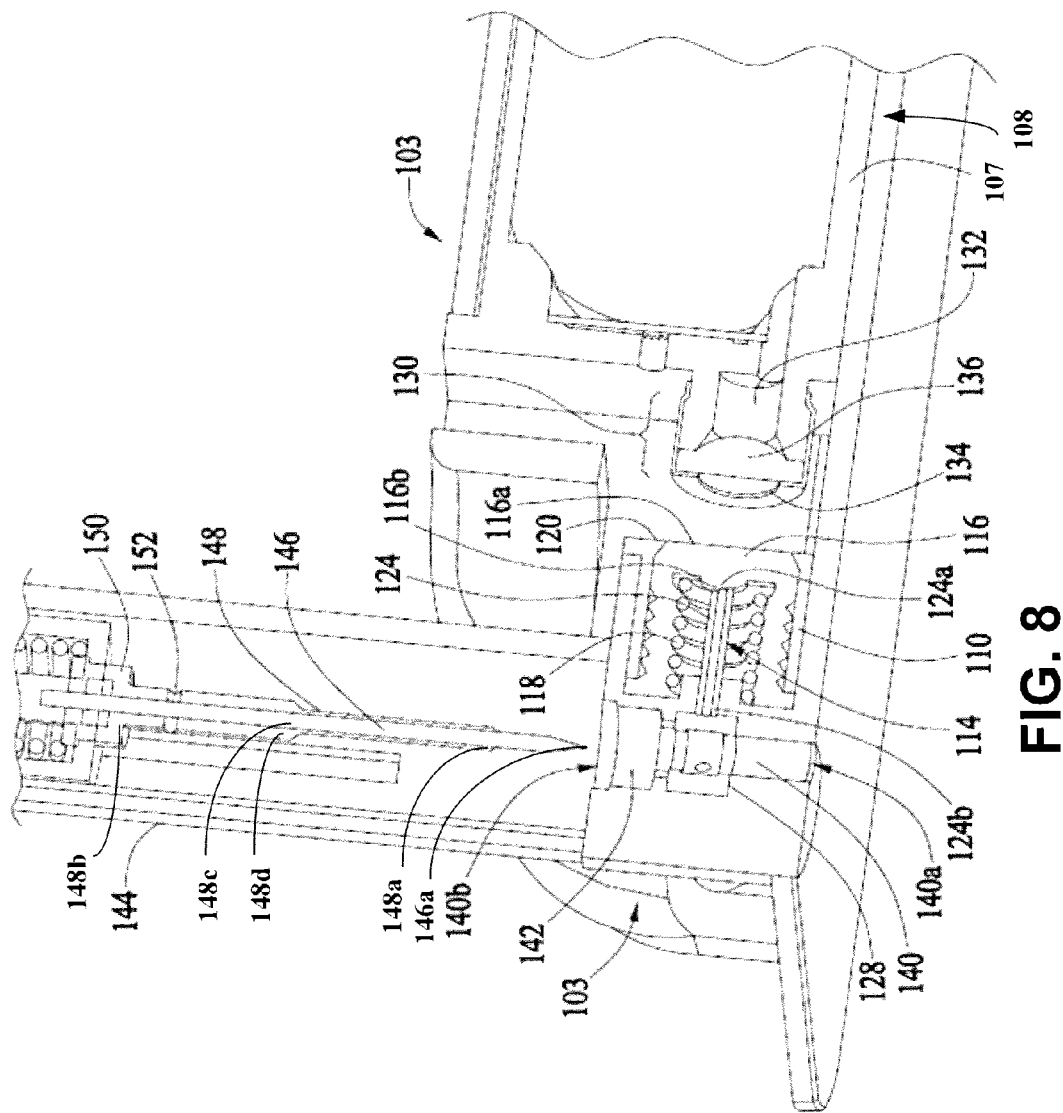
FIG. 8 illustrates a medical device in accordance with an embodiment of the present invention.
Figure 11:
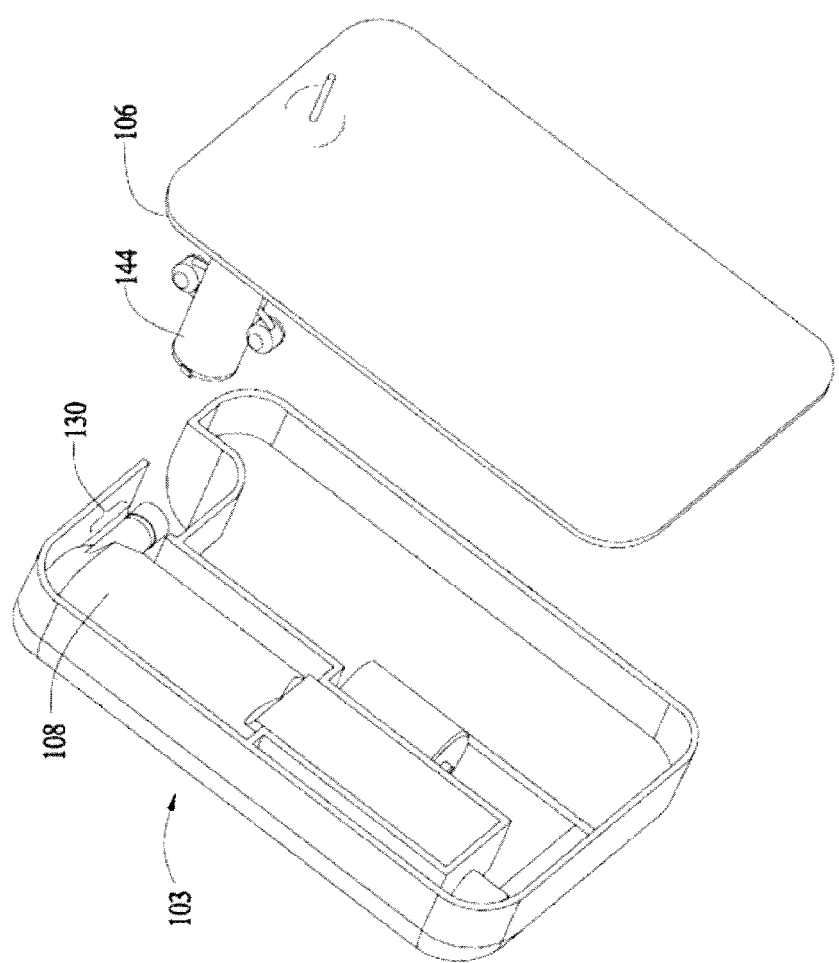
FIG. 11 illustrates a medical device in accordance with an embodiment of the present invention.
Figure 12:
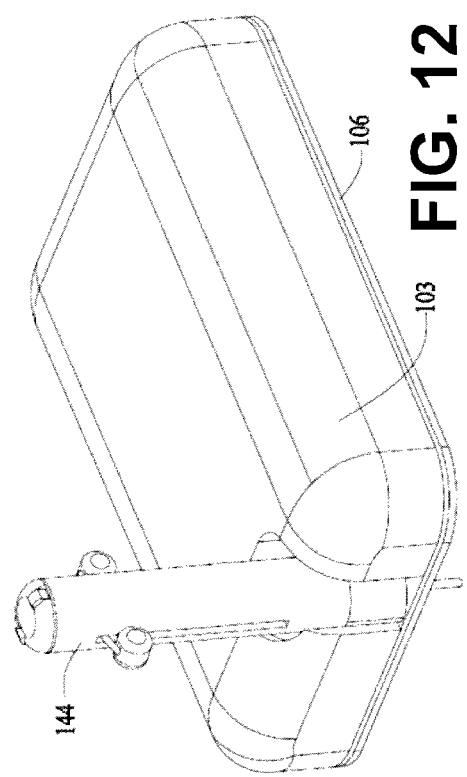
FIG. 12 illustrates a medical device in accordance with an embodiment of the present invention.

The connection portion 130 of the housing 108 may have a suitable shape and size to fit at least partially within the opening 112 of the receptacle structure 110 in the first member 102 when the first member 102 and the second member 103 are connected together. In the drawings of FIGS. 7 and 8, the first member 102 and the second member 103 are shown in a separated, disconnected relation, wherein the connection portion 130 of the housing 108 is outside of the opening 112 of the receptacle structure 110. By moving the first member 102 and the second member 103 together to insert the connection portion 130 into the opening 112 of the housing 108 an end surface of the connection portion 130 may be urged against the first septum 116. This may cause the moveable first septum 116 to move relative to the housing 108 against the force of the bias mechanism 118 toward the interior of the chamber 114. As the first septum 116 is moved toward the interior of the housing 108, the sharp end 124a of the needle 124 may pierce the first septum 116. Continued relative movement of the first member 102 and the second member 103 together may cause the sharp end 124a of the needle 124 to pass through the first septum 116 in the first member 102, then pierce, and pass through the second septum 136 in the second member 103.

When the first member 102 and the second member 103 are brought together (e.g., FIG. 9), at least a portion of the connection portion 130 may extend inside of the receptacle structure 110. With reference to FIGS. 8 and 9, the needle 124 may pierce the first septum 116 and the second septum 136 to form a fluid flow path between the interior chamber 132 of the connection portion 130 and the manifold 128 or other structure at the opening 124b of the needle 124. The receptacle structure 110 and the connection portion 130 may be provided with mating connectors that provide, for example, a snap or friction connection upon the first member 102 and the second member 103 being brought together as shown in FIG. 9. In some embodiments, the mating connectors may include a protrusion (not shown) on one or the other of the receptacle structure 110 and the connection portion 130. The other of the receptacle structure 110 and the connection portion 130 may include a groove or indentation (not shown) arranged to engage each other in a snap-fitting manner upon the connection portion 130 being extended into the receptacle structure 110 a suitable distance.

As mentioned above, in some embodiments, the opening 124b of the needle 124 may be connected in fluid flow communication with the manifold 128 in the injection site section 105. The injection site section 105 may include a channel 140 extending through the housing 104 and the base 106. The channel 140 may have an open end 140a on a bottom surface (relative to the orientation shown in FIG. 8) of the base 106. The channel 140 may have another open end 140b at an upper surface (relative to the orientation shown in FIG. 8) of the injection site section 105 of the housing 104.

The manifold 128 may be located along a length of the channel 140 and may be in fluid flow communication with the channel 140. Accordingly, the needle 124 may be arranged in fluid flow communication with the interior of the channel 140 through the manifold 128. The channel 140 may include a channel section 142 having a larger radial dimension relative to a remaining portion of the channel 140 and may have a suitable shape and size to receive a needle and/or cannula, as will be described later. The manifold 128 may be made of a material of suitable strength and durability such as, but not limited to, plastic, metal, glass, or the like.

A needle-inserting device 144 may be located adjacent the open end 140b of the channel 140 and arranged to selectively extend a needle and/or cannula into the open end 140b of the channel 140 and at least partially through the channel 140 as will be described. In various embodiments, the needle-inserting device 144 may be configured to be integral with or otherwise fixed to the section 105 of the housing 104 of the first member 102. In other embodiments, the needle-inserting device 144 may be a separate device from the housing 104 and may be selectively engaged or connected to, for example in alignment with the channel 140 (e.g., FIG. 8), and disengaged or disconnected from the injection site section 105 of the housing 104.

In embodiments in which the needle-inserting device 144 is a separate structure that connects to and disconnects from the injection site section 105, a suitable connection structure may be provided on the needle-inserting device 144 and/or the injection site section 105 to provide a manually releasable connection between those components. For example, the connection structure may include, but is not limited to, a threaded extension on one or the other of the needle-inserting device 144 and the injection site section 105 and a corresponding threaded receptacle on the other of the injection site section 105 and the needle-inserting device 144 for receiving and mating with the threaded extension in threaded engagement. In other embodiments, other suitable connection structures may be employed, including, but not limited to, flexible pawls or extensions on one or the other of the needle-inserting device 144 and the injection site section 105 and a corresponding aperture, stop surface, or the like on the other of the injection site section 105 and the needle-inserting device 144 or friction fitting engageable portions on each of the section 105 and needle-inserting device 144.

In the drawing of FIG. 8, the needle-inserting device 144 is shown as connected to the injection site section 105 with a needle 146 and a cannula 148 in a retracted state. With reference to FIGS. 7-12, the needle-inserting device 144 may be operated to selectively move the needle 146 and the cannula 148 from the retracted state (e.g., FIG. 8) to an extended state (e.g., FIG. 13) in which the needle 146 and the cannula 148 extend through the opening 140*b* of the channel 140 and at least partially through the channel 140 such that a sharp end 146*a* of the needle 146 and at least a portion of the length of the cannula 148 extend out the opening 140*a* of the channel 140.

Various examples of suitable structures for needle-inserting devices are described in U.S. patent application Ser. No. 11/645,435, filed Dec. 26, 2006, entitled "Infusion Medium Delivery System, Device And Method With Needle Inserter And Needle Inserter Device And Method," which is assigned to the assignee of the present invention and is incorporated herein by reference in its entirety. Further examples of various needle-inserting devices are described in, but are not limited to, U.S. patent application Ser. No. 11/645,972, filed Dec. 26, 2006, "Infusion Medium Delivery System, Device And Method With Needle Inserter And Needle Inserter Device And Method"; U.S. patent application Ser. No. 11/646,052, filed Dec. 26, 2006, "Infusion Medium Delivery System, Device And Method With Needle Inserter And Needle Inserter Device And Method"; U.S. patent application Ser. No. 11/645,435, filed Dec. 26, 2006, "Infusion Medium Delivery System, Device And Method With Needle Inserter And Needle Inserter Device And Method"; U.S. patent application Ser. No. 11/646,000, filed Dec. 26, 2006, "Infusion Medium Delivery System, Device And Method With Needle Inserter And Needle Inserter Device And Method,", all of which are herein incorporated by reference in its entirety. Other examples of suitable structures for needle-inserting devices are described herein.

The cannula 148 may have a hollow central channel 148*c* extending along a longitudinal length of the cannula 148 and open at one end 148*a* that may be adjacent the sharp end 146*a* of the needle 146. An end 148*b* of the cannula 148 opposite the open end 148*a* may have a head 150 having a larger radial dimension than a shaft portion 148*d* of the cannula 148. The cannula head 150 may have a suitable shape and size to fit into the channel section 142 of the channel 140 when the needle 146 and the cannula 148 are moved to the extended state by the needle-inserting device 144.

In particular embodiments, the cannula head 150 may include one or more protrusions and/or indentations for engaging one or more corresponding indentations and/or protrusions in the channel section 142 of the injection site section 105 to provide a friction fit, snap fit, or the like. Accordingly, the cannula 148 may be locked or retained within the injection site section 105 upon the needle 146 and cannula 148 being moved to the extended state by the needle-inserting device 144. In further embodiments, instead of or in addition to engaging protrusions and indentations, one or more other mechanical structures may be employed to provide a suitable retaining function for retaining the cannula 148 in place within the injection site section 105, including, but not limited to, a friction fit structure, snap fit, or the like.

The cannula 148 may have a connection channel 152 provided in fluid flow communication with the hollow central channel 148*c* of the cannula 148. The connection channel 152 may be provided along the longitudinal length of the cannula 148 at a location at which the connection channel 152 aligns with the manifold 128 (i.e., in fluid flow communication with an interior of the manifold 128) when the needle 146 and the cannula 148 have been moved to the extended state by the needle-inserting device 144. In this manner, upon the cannula 148 being moved to the extended state, the hollow central channel 148*c* of the cannula 148 may be arranged in fluid flow communication with the reservoir 108 through the manifold 128 and the connection channel 152.

Thus, according to some embodiments, in operation, a first member 102, which may include, for example, a housing 104 having a receptacle 110 and an injection site section 105, may be coupled together with a second member 103, which may include, for example, a housing 108 having a reservoir 107. The first member 102 may be coupled or otherwise operatively connected, by inserting a connection portion 130 of the second member 103 into a receptacle 110 of the first member 102. Upon coupling the first member 102 and the second member 103, fluid flow communication may be provided between the second member 103 and the injection site section 105 in the first member 102.

In various embodiments, the needle-inserting device 144 may be coupled to the injection site section 105 of the housing 104 of the first member 102 or may be provided as part of a single, unitary structure (i.e., integral) with the injection site section 105 of the housing 104. In some embodiments, the base 106 of the first member 102 may be secured to skin of a user-patient at a suitable injection location with, for example, but not limited to, adhesive material as described in U.S. patent application Ser. No. 11/645,435, filed Dec. 26, 2006, entitled "Infusion Medium Delivery system, Device And Method With Needle Inserter And Needle Inserter Device And Method," and/or as described herein. Alternatively or in addition, the base 106 may be secured to the user-patient by one or more other suitable structures, including, but not limited to, straps, or the like.

Once the base 106 is suitably secured to the skin of the user-patient at a suitable injection location, the inserting device 144 may be actuated to move the needle 146 and the cannula 148 from a retracted state (e.g., FIG. 8) to an extended state. In the extended state, the needle 146 and/or the cannula 148 may pierce the skin of the user-patient adjacent the base 106. The cannula 148 may be locked into its extended state by engagement of the cannula head 150 and the channel section 142, as previously described.

With the cannula 148 locked in the extended state, the needle 146 may be retracted, for example, by automatic operation of the needle-inserting device 144 and/or by manual removal of the needle-inserting device 144 from the injection site section 105. Once the needle 146 is removed, the cannula 148 may be held in place by the injection site section 105 with a portion of the cannula 148 extending into the user-patient. As such, the cannula 148 may be connected in fluid-flow communication with the needle 124. Accordingly, by connecting the first member 102 and the second member 103, as described above, then a fluid-flow connection may be provided from the reservoir 107 to the cannula 148 through the needle 124 and the manifold 128.

A connection sequence (e.g., the sequence of connecting the needle-inserting device 144 to the injection site section 105 of the housing 104, connecting the receptacle 110 of the housing 104 to the connection portion 130 of the housing 108 having the reservoir 107, and connecting the base 106 of the first member 102 to the skin of the user-patient) for connecting various components may be different for different embodiments. In some embodiments, the user-patient may be provided with a first member 102 having a base 106, a housing 104, and an injection site section 105 in a pre-connected state with the needle-inserting device 144. In this manner, a user-patient need not have to connect the needle-inserting device 144 to the housing 104 as those parts are supplied to the user in a pre-connected state, for example, from a manufacturing or assembly facility. In such embodiments, the base 106 of the first member 102 may be secured to skin of the user-patient at a suitable injection location. After securing the base 106 to the skin of the user-patient, the needle-inserting device 144 may be activated to cause the needle 146 and the cannula 148 to be moved to the extended state and pierce the skin of the user-patient.

After activation of the needle-inserting device 144, the needle-inserting device 144 may be removed from the injection site section 105, thus leaving the cannula 148 in place within the injection site section 105 and partially extended into the user-patient. With the base 106 of the first member 102 secured to the skin of the user-patient and the cannula 148 inserted at least partially into the user-patient and arranged in fluid-flow communication with the needle 124, the second member 103 may be connected to the first member 102. In particular, the connection portion 130 of the housing 108 of the second member 103 may be inserted into the receptacle 110 of the housing 104 of the first member 102 to provide a fluid-flow connection between the interior of the housing 108 and the needle 124 and, thus, the cannula 148. Accordingly, the housing 108, which may include the reservoir 107, for example, may be coupled in fluid-flow communication with the cannula 148 that has been extended into the user-patient for delivering fluid from the reservoir 107 to the user-patient. In other embodiments, such a connection may be for conveying fluid from the user-patient to the reservoir 107.

While the connection sequence in some of the above embodiments involve securing the base 106 of the first member 102 to the user-patient prior to connection of the second member 103 to the first member 102, in other embodiments, the second member 103 may be connected to the first member 102, as described above, prior to securing the base 106 of the first member 102 onto the skin of the user-patient. In such embodiments, the first member 102 and the second member 103 may be connected together and, thereafter, may be secured to the user-patient, for example, by adhering one or both of the first member 102 and the second member 103 to the skin of the user-patient. In addition, while the connection sequence in the above embodiments involve activating the needle-inserting device 144 prior to the connection of the second member 103 to the first member 102, in other embodiments, the second member 103 may be connected to the first member 102, as described above, prior to activating the needle-inserting device 144.

In some embodiments, such as the embodiments shown in FIGS. 7 and 8, the receptacle 110 may be in the first member 102 and the connection portion 130 may be in the second member 103. In other embodiments, the receptacle 110 may be in the second member 103, for example, in or associated with a housing for a reservoir and the connection portion 130 may be in the first member 102, for example, in or associated with a housing containing an injection site structure.

In some embodiments, such as the embodiments shown in FIGS. 7 and 8, the receptacle 110 may be arranged to allow the connection portion 130 of the second member 103 to be inserted in a direction substantially parallel to a plane of an upper-facing (in the orientation of FIG. 7) surface of the base 106. For example, in the orientation of FIG. 7, the direction of insertion is shown as a horizontal direction of relative motion between the first member 102 and the second member 103.

Again referring to FIGS. 7 and 8, in other embodiments, the receptacle 110 may be arranged in other suitable orientations, including, but not limited to, an orientation allowing an insertion direction (i.e., relative motion of the first member 102 and the second member 103) to be substantially perpendicular to the plane of the upper-facing surface of the base 106. In yet other embodiments, the receptacle 110 may be arranged to allow any other suitable insertion direction at a non-perpendicular angle transverse to the plane of the upper-facing surface of the base 106.

FIGS. 13-17 illustrate a fluid connection system 201 that may be employed as an embodiment of the structure 100 (e.g., FIGS. 7-12) discussed above in accordance with an embodiment of the present invention. Although the fluid connection system 201 may be similar or used with the embodiments of FIGS. 1-12, it should be understood that the fluid connection system 201 may also include some or all of the same components and operate in a manner similar to that shown and described in the embodiments of FIGS. 18-22. In addition, some or all of the features shown in FIGS. 1-12 may be combined in various ways and included in the embodiments shown in FIGS. 18-22. Likewise, it should be understood that any of the features of the embodiments of FIGS. 13-17 may be combined or otherwise incorporated into any of the other embodiments of FIGS. 13-17 as well as any other embodiment herein discussed. Also, the fluid connection system 201 may be employed or used with other types of delivery device systems other than those described in the disclosure. In various embodiments, the fluid connection system 201 may be employed with a medical device 200.

In FIGS. 13-17, an example of a fluid connection system 201 and method for connecting two members in fluid flow communication is described with reference to a first member 202 and a second member 203. The first member 202 may include a housing 204 on a base 206. The housing 204 may be formed integral with the base 206 or may be formed as a separate structure connected to the base 206 in a fixed relation to the base 206. The housing 204 and the base 206 each may be made of any suitably rigid material, including, but not limited to plastic, metal, ceramic, composite material, or the like.

The housing 204 may include an injection site section 205 containing an injection site structure in which a hollow needle or cannula may be inserted into a user-patient for conveying fluidic media to or from the user-patient. The housing 204 may be made of a material of suitable strength and durability such as, but not limited to, plastic, metal, glass, or the like. In other embodiments, instead of or in addition to an injection site, the housing 204 may contain, be part of, or be operatively connected to any other suitable structure for conveying, containing, and/or processing fluidic media.

The second member 203 may also include a housing 208, which in the illustrated embodiment may include a reservoir 207 for containing fluidic media. The reservoir 207 may be configured and/or made of materials as previously described with respect to the reservoir system 40 (e.g., FIGS. 1-6C). The second member 203 may be held within or otherwise be covered by an housing 209 configured to attach to the base 206. The housing 209 may be configured to connect to the base 206 of the first member 202 by any suitable connection structure. In some embodiments, the housing 209 may be the durable housing 30 (e.g., FIGS. 1-6C). In such embodiments, for example, the housing 209 may include various circuitry or drive devices (e.g., drive device 80) or the like. In some embodiments, the second member 203 may be (or may include) the disposable portion 20 (e.g., FIGS. 1-6C). In some embodiments, the connection portion 230 may be a connection portion (or "port" portion of the reservoir 207).

In particular embodiments, at least one of the housing 209 and the base 206 may include one or more flexible pawls, protrusions, indentations, or the like for engaging and/or receiving one or more corresponding pawls, protrusions, indentations, or the like on the other of the base 206 and the housing 209 to provide a suitable connection structure. Alternatively or in addition, the connection structure may include adhesive material or other suitable connectors.

In other embodiments, the housing 208 may be or be connected to a sensor housing (not shown) containing sensor components. In yet other embodiments, the housing 208 may contain, be part of, or be operatively connected to any other suitable structure for conveying, containing, and/or processing fluidic media. The housing 208 may be made of any suitably rigid material, including, but not limited to, plastic, metal, ceramic, composite material, or the like.

The housing 204 may have or be connected to a receptacle structure 210. The receptacle structure 210 may have an opening 212 leading into a chamber 214 within the receptacle structure 210. In some embodiments, the receptacle structure 210 may be part of the housing 204 adjacent a section of the housing 204 containing the injection site section 205. In other embodiments, the receptacle structure 210 may include a further housing connected to the housing 204.

Each of the connection portion 230 and the receptacle structure 210 may be sized and shape to allow the receptacle structure 210 to receive the connection portion 230. For example, in some embodiments, each of the connection portion 230 and the receptacle structure 210 may be round in shape with the receptacle structure 210 having a larger diameter to allow the connection portion 230 to fit within the receptacle structure. However, in other embodiments, the connection portion 230 and/or the receptacle structure 210 may be sized and shaped in any suitable manner. Furthermore, each of the connection portion 230 and the receptacle structure 210 may have different shapes. For example, the receptacle structure 210 may have a square opening for receiving a round connection portion 230. The square opening may be as wide as a diameter of the round connection portion 230.

A needle 224 may be supported within the chamber 214. The needle 224 may be hollow and may have an end 224a directed toward the opening 212 of the receptacle structure 210. The needle 224 may be supported by a supporting structure located within the receptacle structure 210. In some embodiments, the supporting structure may be a wall integral with the receptacle structure 210. The supporting structure may be located, for example, on an opposite end of the chamber 214 relative to the end of the chamber 214 at which the opening 212 is located. In other embodiments, the supporting structure may be any suitable structure that is generally fixed relative to the receptacle structure 210 and is able to support the needle 224 in a generally fixed relation to the receptacle structure 210.

The needle 224 may be made of any suitably rigid material, including, but not limited to metal, plastic, ceramic, or the like, and may have a hollow channel extending in a lengthwise dimension of the needle 224. The hollow channel in the needle 224 may be open on the end 224a of the needle 224 and may be open at another location 224b along the lengthwise dimension of the needle 224, such as, but not limited to, the needle end opposite the end 224a. The hollow channel in the needle 224 may provide a fluid flow path between the end 224a of the needle 224 and the opening 224b of the needle 224. In some embodiments, the opening 224b of the needle 224 may be connected in fluid flow communication with a manifold 228 in the injection site section 205.

The receptacle structure 210 may include a pierceable member 240 configured to protect the needle 224, and thus the flow path connected to the patient-user, from debris or the like. The pierceable member 240 may be located within the chamber 214 with an end 241 of the pierceable member 240 facing the opening 212 of the chamber 214. The pierceable member 240 may include an interior volume 242 in which the needle 224 may be disposed.

In some embodiments, the needle 224 may be supported within the pierceable member 240 such that a longitudinal axial dimension of the needle 224 extends generally parallel to a longitudinal axial dimension of the pierceable member 240. The needle 224 may be arranged in the interior volume 242 of the pierceable member 240 such that the end 224a of the needle 224 faces a front end 241 of the pierceable member 240.

The pierceable member 240 may be configured to be compressible to a first state and expandable to a second state in an accordion-like manner. In particular embodiments, the pierceable member 240 may include a plurality of protrusions or corrugations on at least one of an inner surface and outer surface of the pierceable member 240 to control compression and/or expansion of the pierceable member 240

The pierceable member 240 may be made of any suitable material that may be pierceable by a needle, such as, but not limited to, a natural or synthetic rubber material, silicon, or the like. In some embodiments, the pierceable member 240 may be made of a self-sealing material capable of sealing itself after a needle has pierced the pierceable member 240 and was subsequently withdrawn from the pierceable member 240. In particular embodiments, the pierceable member may be made of a resilient or elastic material (e.g., silicon, elastic material, liquid silicone rubber (LSR)) that provides sufficient structural strength that allows the pierceable member 240 to be compressible (e.g., by the connection portion 230 as will be described) to the first state (from the second state) and expandable to the second state (from the first state), yet minimizing a force on the connection portion 230 as the connection portion 230 compresses the pierceable member 240.

The pierceable member 240 may be supported by a supporting structure (e.g., the structure supporting the needle 224) located within the receptacle structure 210. In some embodiments, the supporting structure may be a wall integral with the receptacle structure 210. The supporting structure may be located, for example, on an opposite end of the chamber 214 relative to the end of the chamber 214 at which the opening 212 is located. In other embodiments, the supporting structure may be any suitable structure that is generally fixed relative to the receptacle structure 210 and is able to support the pierceable member 240 in a generally fixed relation to the receptacle structure 210.

The housing 208 of the second member 203 may include a connection portion 230 having a hollow interior chamber 232 and an opening 234 into the interior chamber 232. A septum 236 may be supported by the housing 208 to seal the opening 234. The septum 236 may be supported in a fixed relation to the housing 208, for example, within the housing 208 at one end of the interior chamber 232.

Figure 13:
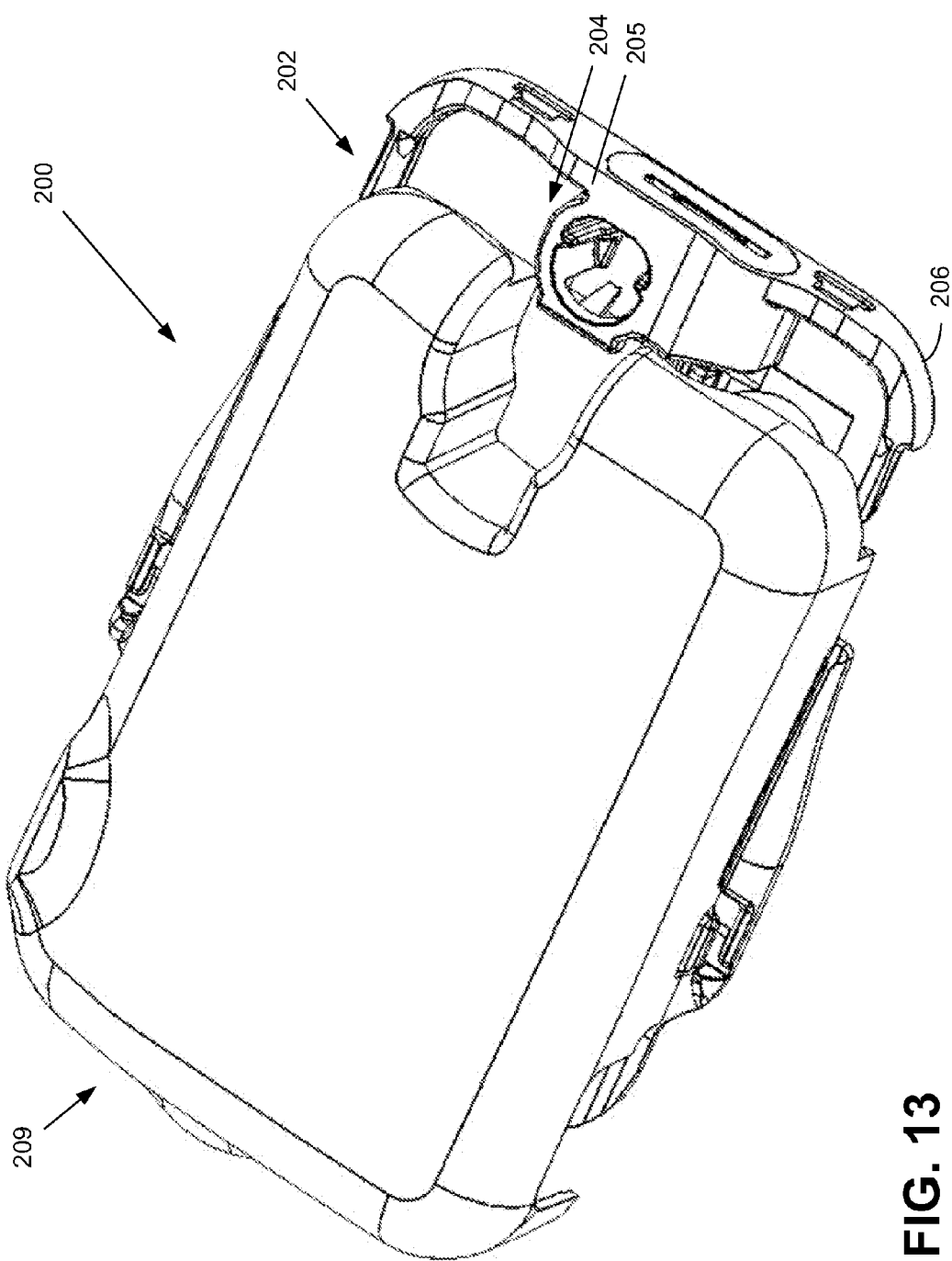
FIG. 13 illustrates a medical device in accordance with an embodiment of the present invention.
Figure 14:
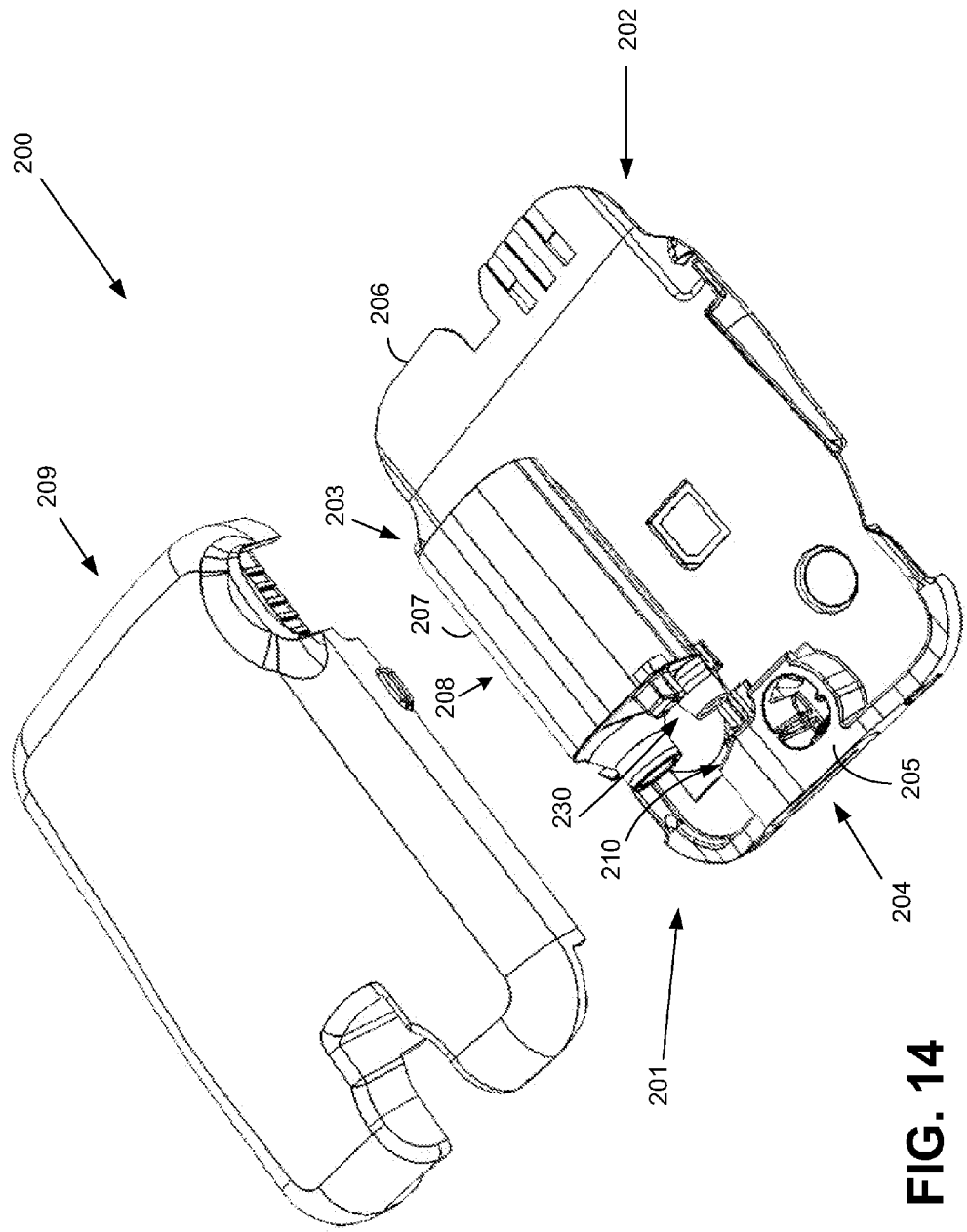
FIG. 14 illustrates a portion of a medical device in accordance with an embodiment of the present invention.
Figure 15:
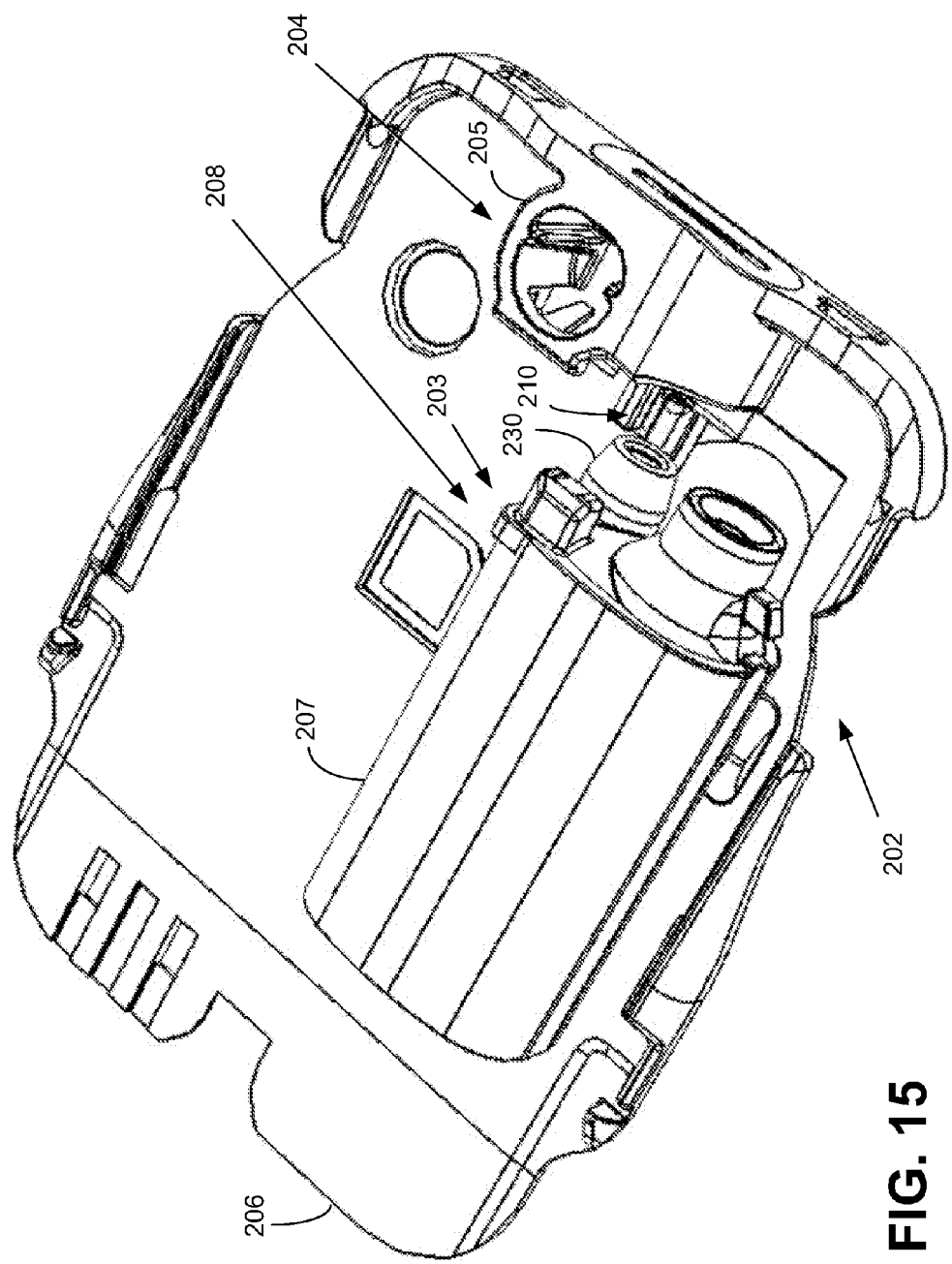
FIG. 15 illustrates a portion of a medical device in accordance with an embodiment of the present invention.
Figure 16:
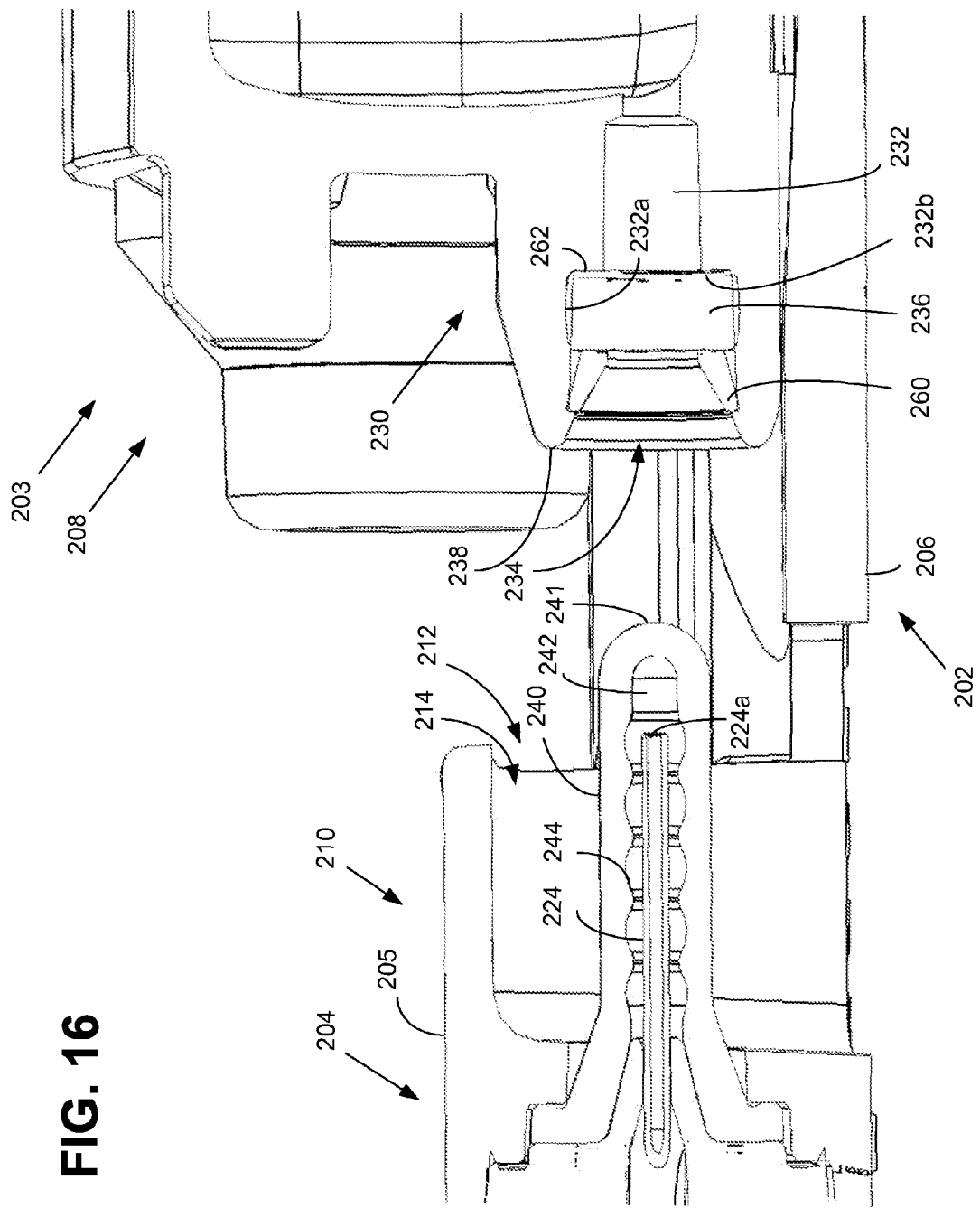
FIG. 16 illustrates a portion of a medical device in accordance with an embodiment of the present invention.
Figure 17:
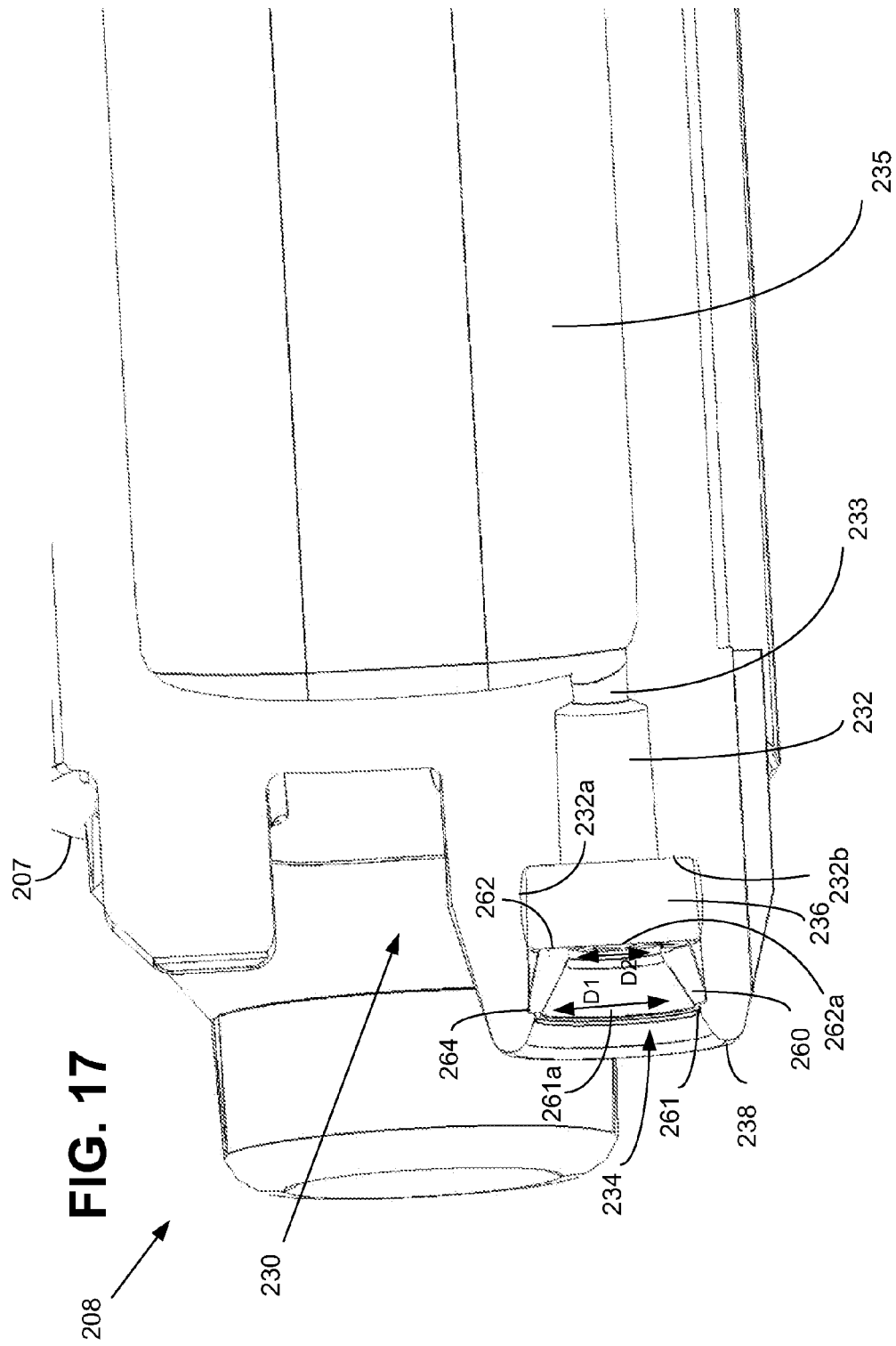
FIG. 17 illustrates a portion of a medical device in accordance with an embodiment of the present invention.
Figure 18:
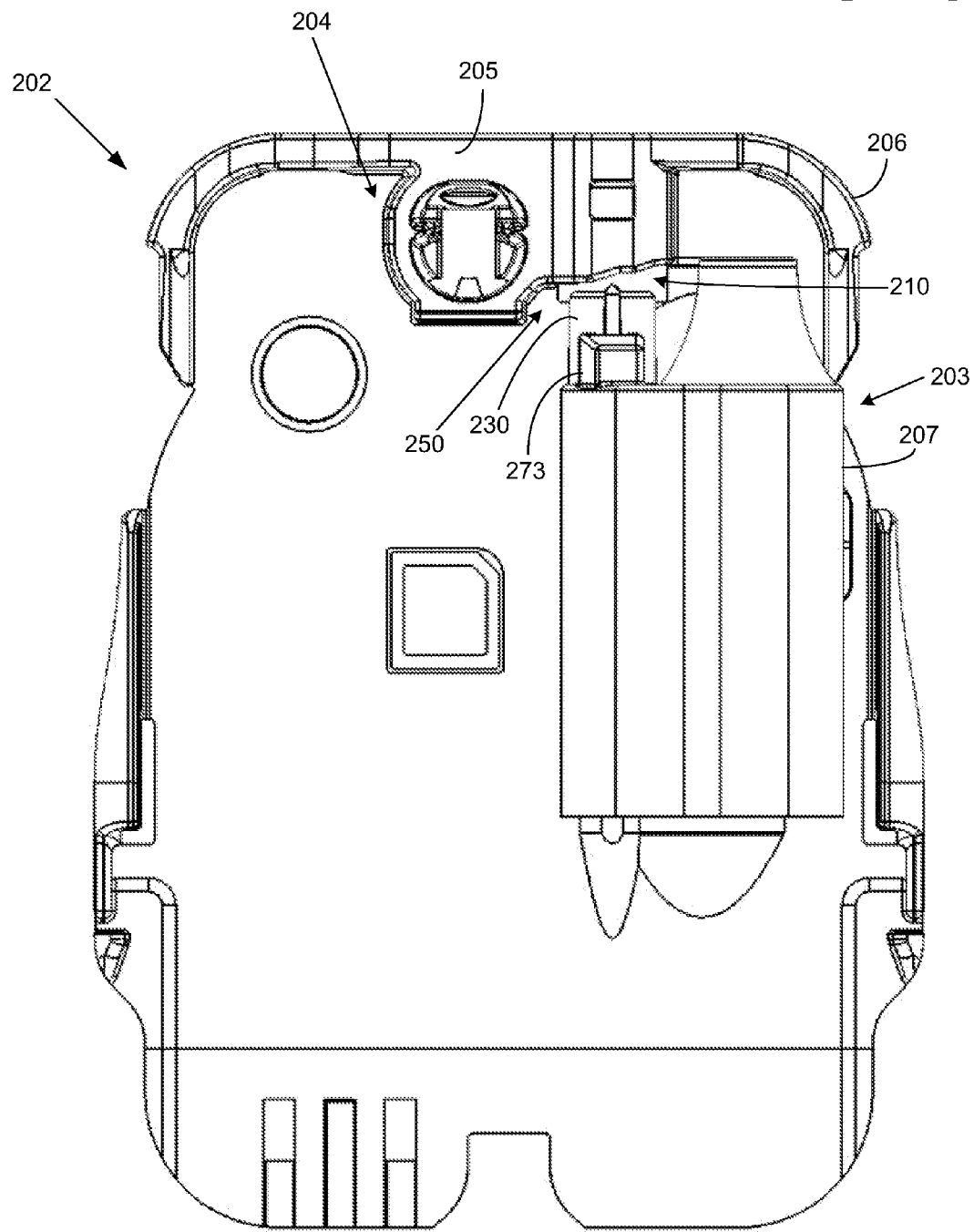
FIG. 18 illustrates a portion of a medical device in accordance with an embodiment of the present invention.

The connection portion 230 of the housing 208 may have a suitable shape and size to fit at least partially within the opening 212 of the receptacle structure 210 in the first member 202 when the first member 202 and the second member 203 are connected together. In the drawings of FIGS. 13, 15, and 16, the first member 202 and the second member 203 are shown in a separated, disconnected relation, wherein the connection portion 230 of the housing 208 is outside of the opening 212 of the receptacle structure 210. By moving the first member 202 and the second member 203 together to insert the connection portion 230 into the opening 212 of the housing 208 an end surface of the connection portion 230 may be urged against the pierceable member 240. This may cause the pierceable member 240 to move relative to the housing 208. As the pierceable member 240 is moved toward the interior of the housing 208, the end 224a of the needle 224 may pierce the pierceable member 240. Continued relative movement of the first member 202 and the second member 203 together may cause the end 224a of the needle 224 to pass through the pierceable member 240 in the first member 202, then pierce, and pass through the septum 236 in the second member 203.

When the first member 202 and the second member 203 are brought together (e.g., FIG. 9), at least a portion of the connection portion 230 may extend inside of the receptacle structure 210. The needle 224 may pierce the pierceable member 240 and the septum 236 to form a fluid flow path between the interior chamber 232 of the connection portion 230 and the manifold 228 or other structure at the opening 224b of the needle 224. The receptacle structure 210 and the connection portion 230 may be provided with mating connectors that provide, for example, a snap or friction connection upon the first member 202 and the second member 203 being brought together (e.g., FIG. 9). In some embodiments, the mating connectors may include a protrusion (not shown) on one or the other of the receptacle structure 210 and the connection portion 230. The other of the receptacle structure 210 and the connection portion 230 may include a groove or indentation (not shown) arranged to engage each other in a snap-fitting manner upon the connection portion 230 being extended into the receptacle structure 210 a suitable distance.

As mentioned above, in some embodiments, the opening 224b of the needle 224 may be connected in fluid flow communication with the manifold (e.g., 128 in FIGS. 7-12) in the injection site section 205, which may be similar to (but not limited to) the injection site section 105 (e.g., FIGS. 7-12). The injection site section 205 may used in combination with an inserting device (e.g., 144 in FIGS. 7-12) for inserting a needle and/or cannula into the patient-user to establish a fluid path between the reservoir 207 and the patient-user, via the injection site section 205.

Various non-limiting examples of suitable structures for needle-inserting devices are described in U.S. patent application Ser. No. 11/645,435, filed Dec. 26, 2006, entitled "Infusion Medium Delivery System, Device And Method With Needle Inserter And Needle Inserter Device And Method," which is assigned to the assignee of the present invention and is incorporated herein by reference in its entirety. Further examples of various needle-inserting devices are described in, but are not limited to, U.S. patent application Ser. No. 11/645,972, filed Dec. 26, 2006, "Infusion Medium Delivery System, Device And Method With Needle Inserter And Needle Inserter Device And Method"; U.S. patent application Ser. No. 11/646,052, filed Dec. 26, 2006, "Infusion Medium Delivery System, Device And Method With Needle Inserter And Needle Inserter Device And Method"; U.S. patent application Ser. No. 11/645,435, filed Dec. 26, 2006, "Infusion Medium Delivery System, Device And Method With Needle Inserter And Needle Inserter Device And Method"; U.S. patent application Ser. No. 11/646,000, filed Dec. 26, 2006, "Infusion Medium Delivery System, Device And Method With Needle Inserter And Needle Inserter Device And Method," all of which are herein incorporated by reference in its entirety. Other examples of suitable structures for needle-inserting devices are described herein.

Thus, according to some embodiments, in operation, a first member 202, which may include, for example, a housing 204 having a receptacle 210 and an injection site section 205, may be coupled together with a second member 203, which may include, for example, a housing 208 having a reservoir 207. The first member 202 may be coupled or otherwise operatively connected, by inserting a connection portion 230 of the second member 203 into a receptacle 210 of the first member 202. Upon coupling the first member 202 and the second member 203, fluid flow communication may be provided between the second member 203 and the injection site section 205 in the first member 202.

In various embodiments, the needle-inserting device may be coupled to the injection site section 205 of the housing 204 of the first member 202 or may be provided as part of a single, unitary structure (i.e., integral) with the injection site section 205 of the housing 204. In some embodiments, the base 206 of the first member 202 may be secured to skin of a user-patient at a suitable injection location with, for example, but not limited to, adhesive material as described in U.S. patent application Ser. No. 11/645,435, filed Dec. 26, 2006, entitled "Infusion Medium Delivery system, Device And Method With Needle Inserter And Needle Inserter Device And Method," and/or as described herein. Alternatively or in addition, the base 206 may be secured to the user-patient by one or more other suitable structures, including, but not limited to, straps, or the like.

Once the base 206 is suitably secured to the skin of the user-patient at a suitable injection location, the inserting device 244 may be actuated to move the needle 246 and the cannula 248 from a retracted state (e.g., FIG. 8) to an extended state. In the extended state, the needle 246 and/or the cannula 248 may pierce the skin of the user-patient adjacent the base 206. The cannula 248 may be locked into its extended state by engagement of the cannula head 250 and the channel section 242, as previously described.

With the cannula 248 locked in the extended state, the needle 246 may be retracted, for example, by automatic operation of the needle-inserting device and/or by manual removal of the needle-inserting device from the injection site section 205. Once the needle 246 is removed, the cannula 248 may be held in place by the injection site section 205 with a portion of the cannula 248 extending into the user-patient. As such, the cannula 248 may be connected in fluid-flow communication with the needle 224. Accordingly, by connecting the first member 202 and the second member 203, as described above, then a fluid-flow connection may be provided from the reservoir 207 to the cannula 248 through the needle 224 and the manifold 228.

A connection sequence (e.g., the sequence of connecting the needle-inserting device to the injection site section 205 of the housing 204, connecting the receptacle 210 of the housing 204 to the connection portion 230 of the housing 208 having the reservoir 207, and connecting the base 206 of the first member 202 to the skin of the user-patient) for connecting various components may be different for different embodiments. In some embodiments, the user-patient may be provided with a first member 202 having a base 206, a housing 204, and an injection site section 205 in a pre-connected state with the needle-inserting device 244. In this manner, a user-patient need not have to connect the needle-inserting device 244 to the housing 204 as those parts are supplied to the user in a pre-connected state, for example, from a manufacturing or assembly facility. In such embodiments, the base 206 of the first member 202 may be secured to skin of the user-patient at a suitable injection location. After securing the base 206 to the skin of the user-patient, the needle-inserting device may be activated to cause the needle 246 and the cannula 248 to be moved to the extended state and pierce the skin of the user-patient.

After activation of the needle-inserting device, the needle-inserting device may be removed from the injection site section 205, thus leaving the cannula 248 in place within the injection site section 205 and partially extended into the user-patient. With the base 206 of the first member 202 secured to the skin of the user-patient and the cannula 248 inserted at least partially into the user-patient and arranged in fluid-flow communication with the needle 224, the second member 203 may be connected to the first member 202. In particular, the connection portion 230 of the housing 208 of the second member 203 may be inserted into the receptacle 210 of the housing 204 of the first member 202 to provide a fluid-flow connection between the interior of the housing 208 and the needle 224 and, thus, the cannula 248. Accordingly, the housing 208, which may include the reservoir 207, for example, may be coupled in fluid-flow communication with the cannula 248 that has been extended into the user-patient for delivering fluid from the reservoir 207 to the user-patient. In other embodiments, such a connection may be for conveying fluid from the user-patient to the reservoir 207.

While the connection sequence in some of the above embodiments involve securing the base 206 of the first member 202 to the user-patient prior to connection of the second member 203 to the first member 202, in other embodiments, the second member 203 may be connected to the first member 202, as described above, prior to securing the base 206 of the first member 202 onto the skin of the user-patient. In such embodiments, the first member 202 and the second member 203 may be connected together and, thereafter, may be secured to the user-patient, for example, by adhering one or both of the first member 202 and the second member 203 to the skin of the user-patient. In addition, while the connection sequence in the above embodiments involve activating the needle-inserting device prior to the connection of the second member 103 to the first member 202, in other embodiments, the second member 203 may be connected to the first member 202, as described above, prior to activating the needle-inserting device.

In some embodiments, the receptacle 210 may be in the first member 202 and the connection portion 230 may be in the second member 203 (e.g., FIG. 9). In other embodiments, the receptacle 210 may be in the second member 203, for example, in or associated with a housing for a reservoir and the connection portion 230 may be in the first member 202, for example, in or associated with a housing containing an injection site structure.

In some embodiments, such as the embodiments shown in FIGS. 7 and 8, the receptacle 210 may be arranged to allow the connection portion 230 of the second member 203 to be inserted in a direction substantially parallel to a plane of an upper-facing (in the orientation of FIG. 13) surface of the base 206. For example, in the orientation of FIG. 13, the direction of insertion is shown as a horizontal direction of relative motion between the first member 202 and the second member 203.

Again referring to FIGS. 13-17, in other embodiments, the receptacle 210 may be arranged in other suitable orientations, including, but not limited to, an orientation allowing an insertion direction (i.e., relative motion of the first member 202 and the second member 203) to be substantially perpendicular to the plane of the upper-facing surface of the base 206. In yet other embodiments, the receptacle 210 may be arranged to allow any other suitable insertion direction at a non-perpendicular angle that is transverse to the plane of the upper-facing surface of the base 206.

In some embodiments, the end 224a of the needle 224 may be blunt. Such embodiments may reduce cost of the needle 224, increase length of the needle 224 for penetration of the septum 236, reduce likelihood that end 224a of the needle 224 is damaged, and/or increase durability of the septum 236. In further embodiments, the septum 236 may include a slit (not shown) or may be perforated before use to allow the blunt end 224a of the needle to pass through the slit of the septum 236. As a result, force on the septum 236 from the needle 224 may be minimized, and thus compression of the septum 236 may be minimized. The slit may have a diameter substantially equal to that of a diameter of the needle 224 to provide sufficient sealing therebetween. In other embodiments, the end 224a of the needle 224 may be beveled or otherwise be sharp. In further embodiments, the septum 216 may include a slit, for example, as previously discussed.

As mentioned, the septum 236 may be arranged in the opening 234 of the connection portion 230. In some embodiments, a guide member, such as a funnel 260 (forming a conical-shaped needle receptacle) or the like, for guiding the needle 224 when the receptacle structure 210 receives the connection portion 230 may be arranged in the opening 234 of the connection portion 230 adjacent the septum 236. In particular, the funnel 260 may guide the needle 224 so that the needle 224 enters the septum 236 in a pre-determined manner (e.g., substantially center of the septum 236). This may help to avoid tearing of the septum 236 as the needle 224 moves laterally through the septum 236, to help avoid leakage around the septum 236 and/or piercing of the needle through the septum 236 and crashing against a wall of the interior chamber 232 of the connection portion 230.

The funnel 260 may be fit within the opening 234 of the connection portion 230 in any suitable manner, for example, with by friction fitting, press fitting, with an adhesive, or the like. In particular embodiments, the funnel 260 may include tabs, barbs 262, or the like for mating or otherwise engaging an inner surface of the connection portion 230 to attach the funnel 260 to the connection portion 230. In other embodiments, the connection portion 260 may include tabs, barbs 264, or the like for mating or otherwise engaging the funnel 260 to help secure the funnel 260 to the connection portion 230. The funnel 260 may be made of any suitably rigid material, such as metal, plastic, composite material, glass, or the like.

A front end 261 of the funnel 260 may define an opening 261a having a diameter D1, and a rear end 262, which may be adjacent the septum 236, of the funnel 260 that may define an opening 262a having a diameter D2. The diameter D1 may be greater than the diameter D2 to allow the needle 224 to be inserted through the opening 261 and then guided through the opening 262.

In some embodiments, the opening 262 may be sized to substantially inhibit the pierceable member 240 from contacting the septum 236 through the opening 262. Thus, for instance, a width of the pierceable member 240 may be less than the diameter D1, but greater than the diameter D2. In such embodiments, when the connection portion 230 is placed in the receptacle structure 210, the funnel 260 may contact and press upon the pierceable member 240 to allow the needle 224 to first pierce the pierceable member 240 and pass through the opening 262a and then pierce the septum 236.

In other embodiments, the opening 262a may be sized to allow at least a portion of the pierceable member 240 to contact the septum 236 through the opening 262a. Thus, for instance, a width of a portion of the pierceable member 240 may be less than the diameter D1, but greater than the diameter D2. In such embodiments, when the connection portion 230 is placed in the receptacle structure 210, the pierceable member 240 may contact the septum 236 through the opening 262a. Accordingly, the septum 236 and/or the funnel 260 may press upon the pierceable member 240 to allow the needle 224 to pierce the pierceable member 240 and pass through the opening 262a to pierce the septum 236.

In various embodiments, the end 224a of the needle 224 should be as close to centerline as possible prior to engagement with the septum 236 to minimize septum 236 damage during insertion. For instance, the diameter D2 may be selected to avoid tearing the septum 236 as the needle 224 pierces or otherwise the septum 236.

In some embodiments, the opening 262a may be sized to guide the needle 224 as it passes through the septum 236 to prevent the needle 224 from contacting the inner surface of the connection portion 230. In particular, the diameter D2 of the funnel 260 may be selected or otherwise configured to prevent the end 224a of the needle 224 from digging or otherwise contact into the inner surfaces of the connection portion 230. In some embodiments, the diameter D2 is less than a diameter of the interior chamber 232 to allow the needle 224 to clear the surfaces defining the interior chamber 232.

In some embodiments, the funnel 260 may be configured to minimize an amount of surface area of the septum 236 that is contacted by the funnel 260. For example, one or more spaces may be provided in the funnel 260. In such embodiments, bulging of the septum 236 when a force is applied to the septum 236, for example by the needle 224 and/or the pierceable member 240 can be controlled. For example, in such embodiments, the septum 236 may bulge into the one or more spaces provided in the funnel 260. As a result, an amount the septum 236 bulges at another location, for example, in toward the interior chamber 232 of the connection portion 230, may be minimized as the septum 236 bulges into the one or more spaces. In other embodiments, spaces (not shown) may be provided in the funnel 260 and/or in the surface 232b of the connection portion 230 supporting the septum 236. Such embodiments may likewise be used to control bulging of the septum 236.

In some embodiments, protrusions (of any suitable shape and/or arrangement) or the like may be provided between the funnel 260 and the septum 236 (and/or the septum 236 and the surface of the connection portion 230) to direct bulging of the septum 236. For instance, the protrusions may be arranged on the funnel 260 to face the septum 236. Thus, the septum 236 may bulge into spaces provided between the protrusions.

In some embodiments, the inner surface 232a of the connection portion 230 may be configured to provide a force on a side surface of the septum 236 to radially compress the septum 236. Such embodiments may cause the septum 236 to "heal" or otherwise fully or partially seal itself after the needle 224 is removed from the septum 236. For example, the inner surface 232 of the connection portion 230 may include one or more protrusions or the like for radially compressing the septum 236.

FIGS. 18-21 illustrate an alignment structure 250 that may be employed with and/or employed as an embodiment of the structures (e.g., 100 in FIGS. 7-12; 201 in FIGS. 13-17) discussed above in accordance with an embodiment of the present invention. Although the alignment structure 250 may be similar or used with the embodiments of FIGS. 7-17, it should be understood that the alignment structure 250 may also include some or all of the same components and operate in a manner similar to that shown and described in the embodiments of FIGS. 1-6C and 22. In addition, some or all of the features shown in FIGS. 1-17 and 17 and 22 may be combined in various ways and included in the embodiments shown in FIG. 18-21. Likewise, it should be understood that any of the features of the embodiments of FIGS. 18-21 may be combined or otherwise incorporated into any of the other embodiments of FIGS. 18-21 as well as any other embodiment herein discussed. Also, the alignment structure 250 may be employed or used with other types of delivery device systems other than those described in the disclosure. In various embodiments, the alignment structure 250 may be employed with the medical device 200 or the like.

With reference to FIGS. 18-21, in some embodiments, the connection portion 230 and the receptacle structure 210 may include an alignment structure 250 for aligning the connection portion 230 and the receptacle structure 210 as the receptacle portion 210 receives the connection portion 230. With reference to FIGS. 13-21, such embodiments may limit amount of relative motion between the first member 202 and the second member 203, may limit offset of the needle 224 as the needle 224 pierces the septum 236 (e.g., to help avoid tearing of the septum 236 and subsequent leakage), and/or may otherwise control how the needle 224 pierces the septum 236 (e.g., to help avoid the needle 224 from crashing into portions of the connection portion 230).

In particular embodiments, the connection portion 230 may include a rib 253, tab, protrusion or the like. The receptacle structure 210 may include a groove 255, recess, or the like for receiving the rib 253 when the receptacle structure 210 receives the connection portion 230. In other embodiments, the connection portion may include the rib 253 and the receptacle structure 210 may include the groove 255.

The rib 253 may be formed as part of the connection portion 230. In other embodiments, the rib 253 may be a separate component attached to the connection portion 230. The groove 255 may be formed as part of the receptacle structure 210. In other embodiments, the groove 255 may be provided on a separate component attached to the receptacle structure 210. The rib 253 may be made of any suitably rigid material, such as (but not limited to) plastic, glass, ceramic, composite material, metal, or the like.

Figure 19:
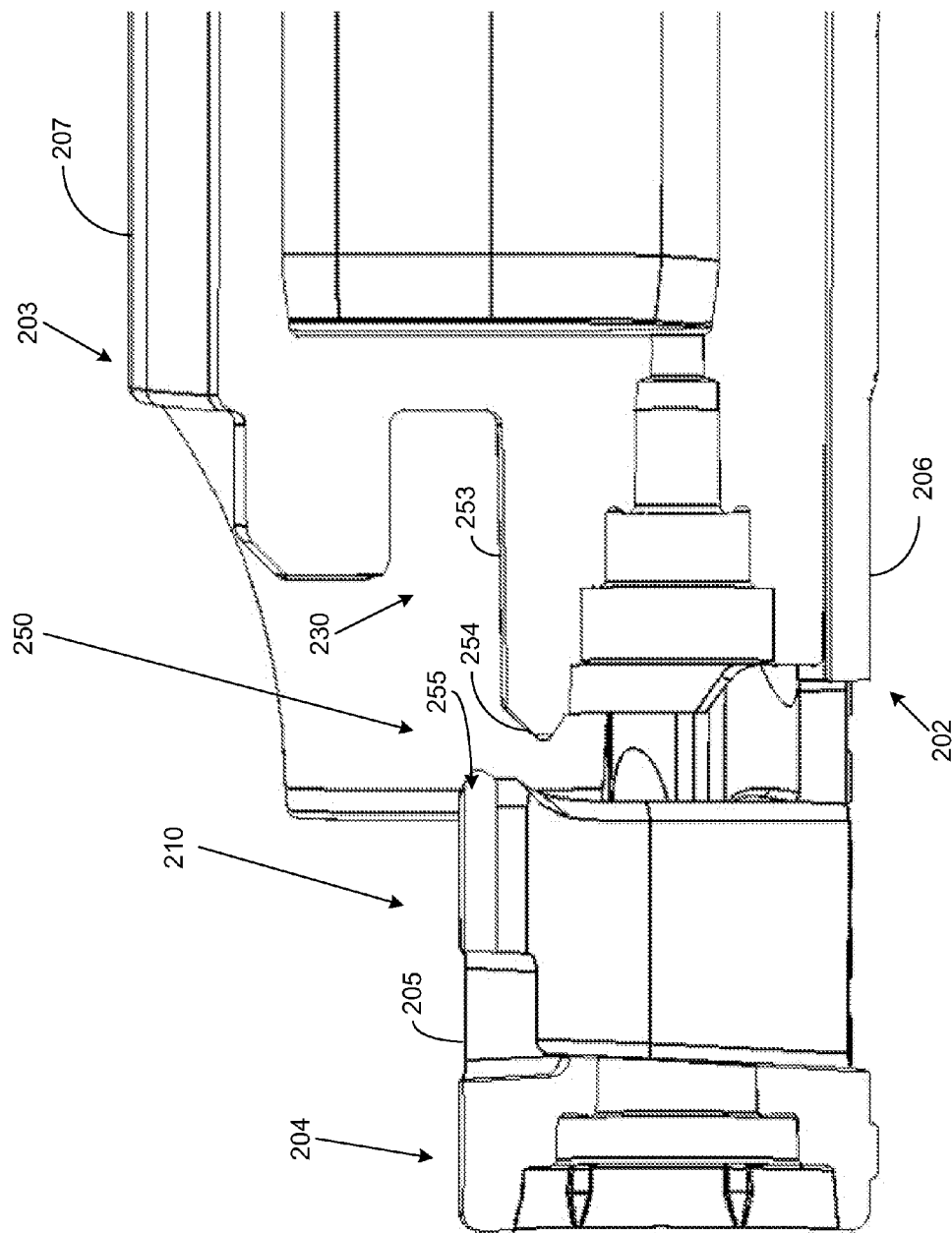
FIG. 19 illustrates a portion of a medical device in accordance with an embodiment of the present invention.
Figure 20:
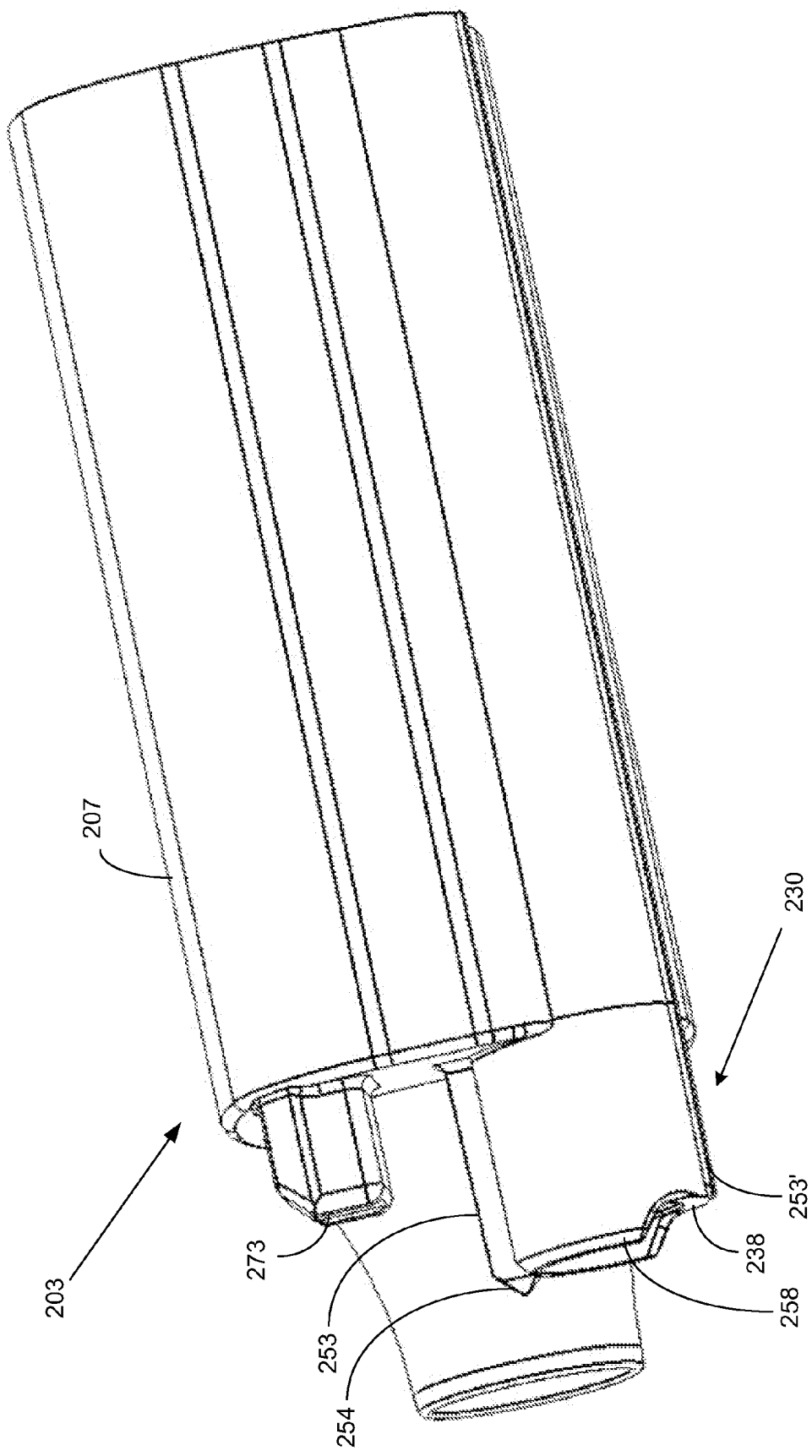
FIG. 20 illustrates a portion of a medical device in accordance with an embodiment of the present invention.
Figure 21:
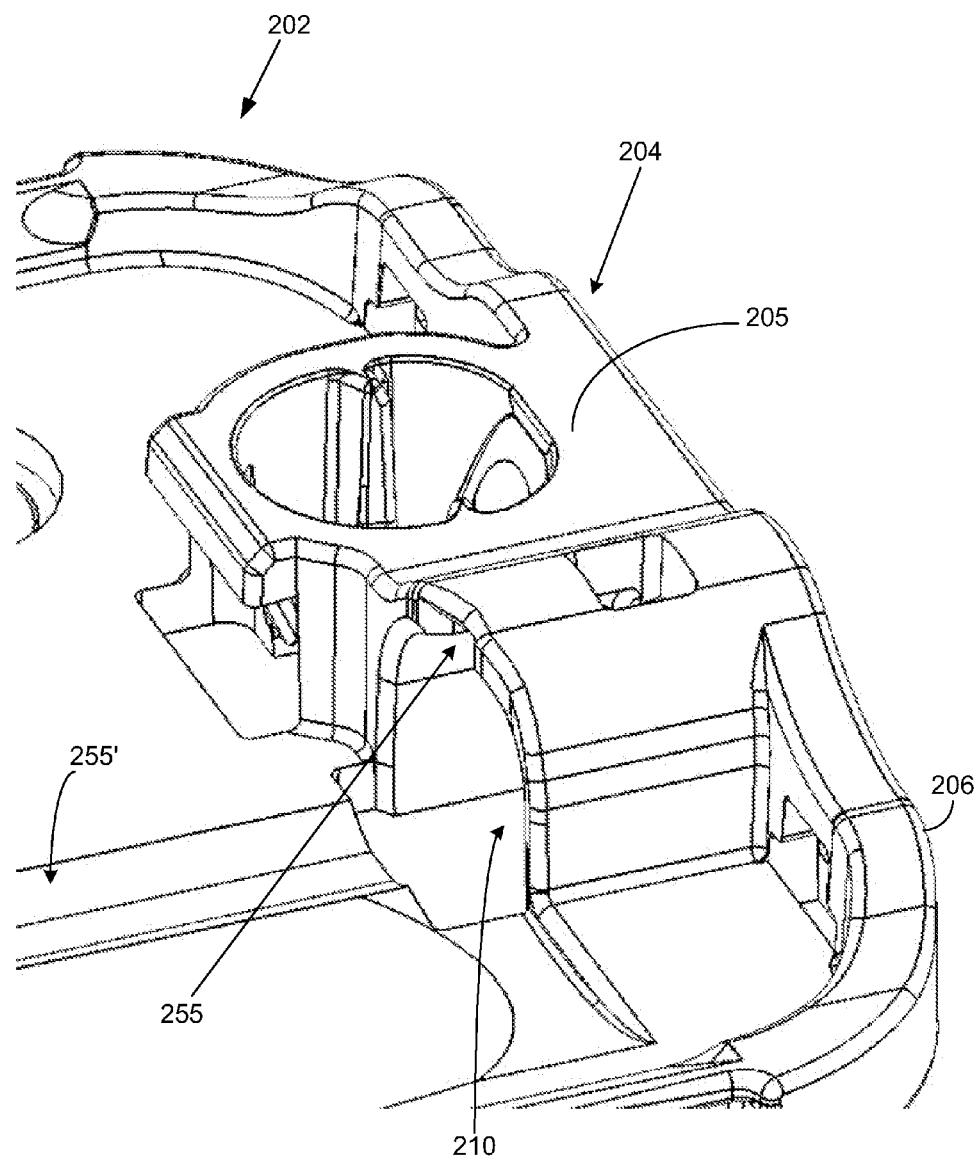
FIG. 21 illustrates a portion of a medical device in accordance with an embodiment of the present invention.

In particular embodiments, the rib 253 may be provided on an upper part of the connection portion 230 (in the orientation of FIG. 19). The groove 255 may be provided on a corresponding portion of the receptacle structure 210 to receive the rib 253 as the receptacle structure 210 receives the connection portion 230. For example, an upper surface of the receptacle structure 210 may include the groove 250. In other embodiments, the rib 253 and the groove 255 may be located along any suitable part of the connection portion 230 and the receptacle structure 210, respectively. In other embodiments, the rib 253 may be provided on the receptacle structure 210 and the groove 255 on the connection portion 230.

In some embodiments, the rib 253 may include a tip portion 254 extending beyond the end surface 238 of the connection portion 230. Accordingly, the tip portion 254 may engage the groove 255 before the receptacle structure 210 receives any portion of the connection portion 230. In further embodiments, the tip portion 254 may extend beyond the end surface 238 at least as much as the pierceable member 240 and/or the needle 224 extends out of the opening 234 of the connection portion 230. Accordingly, the tip portion 254 may engage the groove 255 before the pierceable member 240 and/or the needle 224 enters the receptacle structure 210. In other words, the tip portion 254 may allow for proper alignment of the needle 224 prior to the needle 224 piercing the septum 236.

In further embodiments, the alignment structure of the rib 253 and groove 255 may be employed with other alignment structures, for example, such as those disclosed in (but not limited to) U.S. patent application Ser. No. 12/649,619, filed Dec. 30, 2009, "Alignment Systems And Methods" and U.S. patent application Ser. No. 12/650,378, filed Dec. 30, 2009, "Connection And Alignment Systems And Methods," all of which are herein incorporated by reference. For instance, those other alignment structures may be employed to roughly align the receptacle structure 210 and the connection portion 230 when the two components (or components of which the receptacle structure 210 and connection portion 230 are part) are brought together. Then the rib 253 and the groove 255 may be employed to provide a more accurate alignment of the receptacle structure 210 and the connection portion 230 with continued movement thereof.

In some embodiments, the connection portion 230 may include an additional rib 253' located for example on a lower surface (e.g., in the orientation of FIG. 19) of the connection portion 230. For example, in embodiments where the rib 253 is located on the upper surface (e.g., in the orientation of FIGS. 19 and 18) of the connection portion 230, the additional rib 253' may be located opposite the rib 253. In particular embodiments, the additional rib 253' may be configured to be secured to the first member 202 when the first member 202 and the second member 203 are brought together. For example, the additional rib 253' may be received in a slot 255' or the like in the first member 202 when the first member 202 and the second member 203 are brought together. In some embodiments, the additional rib 253' may be included without the rib 253.

In some embodiments, the connection portion 230 may include a rim 258 or "visor" on the end surface 238 of the connection portion 230 such that the rim 258 extends around at least a portion of the opening 234 of the connection portion 230. The rim 258 may extend from the end surface 238 a distance greater than the amount the pierceable member 240 and the needle 224 extend out of the opening 212 of the receptacle structure 210. Accordingly, the end surface 238 (or any other portion) of the connection portion 230 may be prevented from contacting and damaging the pierceable member 240 and/or the needle 224, for example, when the reservoir 207 is installed to the base 206 or the like. In particular embodiments, the rim 258 may be at least partially chamfered or otherwise have a beveled edge.

Figure 22:
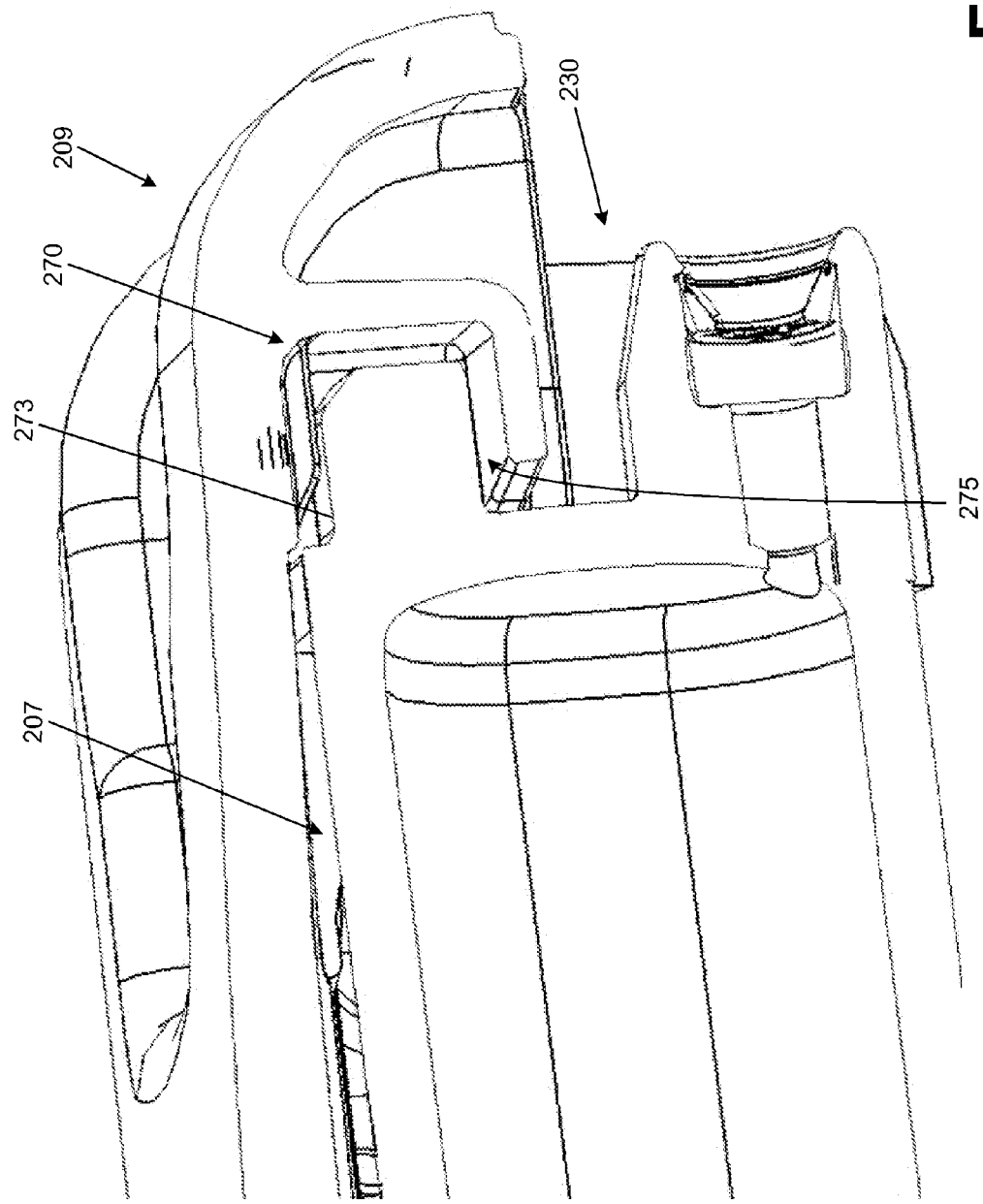
FIG. 22 illustrates a portion of a medical device in accordance with an embodiment of the present invention.

FIG. 22 illustrate an alignment structure 270 that may be employed with and/or employed as an embodiment of the structures (e.g., 100 in FIGS. 7-12; 201 in FIGS. 13-17; 250 in FIGS. 18-21) discussed above in accordance with an embodiment of the present invention. Although the alignment structure 270 may be similar or used with the embodiments of FIGS. 7-21, it should be understood that the alignment structure 270 may also include some or all of the same components and operate in a manner similar to that shown and described in the embodiments of FIGS. 1-6C. In addition, some or all of the features shown in FIGS. 1-21 may be combined in various ways and included in the embodiments shown in FIG. 22. Likewise, it should be understood that any of the features of the embodiments of FIG. 22 may be combined or otherwise incorporated into any of the other embodiments of FIG. 22 as well as any other embodiment herein discussed. Also, the alignment structure 270 may be employed or used with other types of delivery device systems other than those described in the disclosure. In various embodiments, the alignment structure 270 may be employed with the medical device 200 or the like.

In some embodiments, such as the embodiment shown in FIG. 22, the medical device 200 may include the alignment structure 270 for aligning two (or more) members, such as the reservoir 207 (or second member 203) with the housing 209. With reference to FIGS. 13-22, such embodiments, for example, may limit amount of relative motion between the two components (e.g., reservoir 207 and housing 209), may limit offset of the needle 224 as the needle 224 pierces the septum 236 (e.g., to help avoid tearing of the septum 236 and subsequent leakage), and/or otherwise control how the needle 224 pierces the septum 236 (e.g., to help avoid the needle 224 from crashing into portions of the connection portion 230).

In particular embodiments, the reservoir 207 may include a protrusion 273, tab, or the like, for example, on the reservoir 207. The housing 209 may include a receiving body or shroud 275 for receiving the protrusion 273 as the two components are brought together. In other embodiments, the housing 209 portion may include the protrusion 273 and the reservoir 207 may include the shroud 275. The protrusion 273 and/or the shroud 275 may be made of any suitably rigid material, such as, but not limited to, plastic, composite material, ceramic, metal, glass, or the like.

The protrusion 273 may be formed as part of the reservoir 207 (or other portion of the second member 203). In other embodiments, the protrusion 273 may be a separate component attached to the reservoir 207. The shroud 275 may be formed as part of the housing 209. In other embodiments, the shroud 275 may be provided on a separate component attached to the housing 209. In some embodiments, the protrusion 273 may have a beveled or angled shape to facilitate insertion into the shroud 275. In some embodiments, the shroud 275 may be configured to facilitate receiving of the protrusion 273. For instance, the opening of the shroud 275 may be made larger than a diameter of the protrusion 273.

In particular embodiments, the protrusion 273 may be provided on an upper part of the reservoir 207 (in the orientation of FIG. 22). For example, the protrusion 273 may be arranged over the connection portion 230. The shroud 275 may be provided on a corresponding portion of the housing 209 to receive the protrusion 273 as the reservoir 207 and the housing 209 are brought together. Thus in various embodiments, the reservoir 207 of the second member 203 may be inserted into the housing 209 such that the protrusion 273 may be received in the shroud 275 to align the reservoir 207 into propose position. Then, the housing 209 and the second member 203 may be connected and aligned as described in (but not limited to) the disclosure herein.

In further embodiments, the alignment structure 270 may be employed with other alignment structures, for example, such as the alignment structure 250, and/or those disclosed in (but not limited to) U.S. patent application Ser. No. 12/649, 619, filed Dec. 30, 2009, "Alignment Systems And Methods" and U.S. patent application Ser. No. 12/650,378, filed Dec. 30, 2009, "Connection And Alignment Systems And Methods," all of which are herein incorporated by reference. For instance, The alignment structure 270 may be employed to provide alignment of the second member 203 (and the reservoir 207) with the housing 209, for example in the Z-axis. Then, the other alignment structures may be employed to roughly align the receptacle structure 210 and the connection portion 230 when the two components or components of which the receptacle structure 210 and connection portion 230 are part (e.g., the reservoir 207 that is aligned with the housing 209) are brought together. Then the alignment structure 250 may be employed to provide a more accurate alignment of the first member 202 and the second member 203, for example in the X-Y axis, with continued movement of the first member 202 and the second member 203.

The embodiments disclosed herein are to be considered in all respects as illustrative, and not restrictive of the invention. The present invention is in no way limited to the embodiments described above. Various modifications and changes may be made to the embodiments without departing from the spirit and scope of the invention. The scope of the invention is indicated by the attached claims, rather than the embodiments. Various modifications and changes that come within the meaning and range of equivalency of the claims are intended to be within the scope of the invention.

What is claimed is:

1. A fluid delivery system, the fluid delivery system comprising:
    a first member;
    a receptacle structure provided on the first member and defining an interior chamber and an opening into the interior chamber;
    a needle supported within the interior chamber of the receptacle structure, the needle having a piercing end;
    a pierceable member provided within the interior chamber, the pierceable member extending along a longitudinal dimension of the needle;
    a second member for connecting with the first member;
    a connection portion provided on the second member, the connection portion having an interior chamber and an opening into the interior chamber of the connection portion, the connection portion having a size and shape suitable to be received at least partially into the opening of the receptacle structure as the first member and the second member are connected; and
    a septum supported by the connection portion of the second member in a position to cover the opening of the connection portion;
    wherein the pierceable member is arranged to be moved, by the connection portion as the connection portion is received into the opening of the receptacle structure within the interior chamber of the receptacle structure in a direction along the longitudinal dimension of the needle toward the piercing end of the needle to cause the piercing end of the needle to pierce the pierceable member and the septum to establish fluid flow communication between the needle and the interior chamber of the connection portion;
    wherein the receptacle structure is fixed with respect to a base portion; and
    wherein the connection portion of the second member is provided in a housing that is connectable to the base portion.

2. The fluid delivery system as recited in claim 1,
    wherein the pierceable member is collapsible from a first state to a second state; and
    wherein the pierceable member is collapsed from the first state to the second state as the connection portion pushes the pierceable member toward the piercing end of the needle.

3. The fluid delivery system as recited in claim 2,
    wherein the pierceable member is expandable from the second state to the first state; and
    wherein the pierceable member is expanded from the second state to the first state as the connection portion is withdrawn from the opening of the receptacle structure.

4. The fluid delivery system as recited in claim 2, wherein the pierceable member includes a plurality of corrugations to allow the pierceable member to be collapsible.

5. The fluid delivery system as recited in claim 1,
    the pierceable member defining an interior volume extending along the longitudinal dimension of the needle;
    wherein the piercing end of the needle is arranged in the interior volume of the pierceable member.

6. The fluid delivery system as recited in claim 1, the system further comprising:
    a further receptacle supported by the connection portion of the second member in a position to guide the needle as the needle pierces the septum.

7. The fluid delivery system as recited in claim 6,
    the septum having a first surface and a second surface opposite the first surface;
    wherein the septum is positioned in the opening of the connection portion such that the first surface of the septum is pierced by the needle before the second surface of the septum as the first and second members are moved together; and
    wherein the receptacle is positioned adjacent the first surface of the septum.

8. The fluid delivery system as recited in claim 6, wherein the receptacle is a conically-shaped member.

9. The fluid delivery system as recited in claim 1, wherein the septum includes a perforation through which the piercing end of the needle is inserted.

10. The fluid delivery system as recited in claim 1,
    wherein the second member comprises a reservoir for containing fluidic media; and
    wherein the connection portion of the second member comprises a portion of the reservoir.

11. The fluid delivery system as recited in claim 1,
    the needle having a first opening into which fluid may flow and a second opening out of which fluid may flow;
    wherein the second opening of the needle is provided in fluid flow communication with a needle injection site channel; and
    wherein the needle injection site channel has an opening that is connectable to a needle inserting device for receiving at least a portion of a needle from the needle inserting device.

12. The fluid delivery system as recited in claim 11,
    wherein the receptacle structure is fixed with respect to a base portion;
    wherein the connection portion of the second member is provided in a housing that is connectable to the base portion; and
    wherein the housing includes a recess through which a needle inserting device may extend when connected to the opening of the needle injection site channel.

13. The fluid delivery system as recited in claim 1, the system further comprising:
    a groove provided in one of the receptacle structure and the connection portion; and
    a protrusion arranged on the other of the receptacle structure and the connection to be received in the groove of the one of the receptacle structure and the connection portion as the first member and the second member are moved together;
    wherein, upon moving the first member and the second member together, the protrusion is received into the groove and the connection portion is received into the opening of the receptacle structure to cause the piercing end of the needle to pierce the septum to come into fluid flow communication with the interior chamber of the connection portion.

14. The fluid delivery system as recited in claim 13, wherein the protrusion is arranged on the connection portion;
wherein the needle is arranged to extend out of the receptacle structure a first distance; and
wherein the protrusion includes a portion that extends from the connection portion a second distance greater than the first distance that the needle extends out of the receptacle structure.

15. The fluid delivery system as recited in claim 14, wherein the protrusion extends in a same direction as the needle to engage the receptacle before the needle contacts the septum.

16. The fluid delivery system as recited in claim 1, the structure further comprising:
a receptacle provided on a third member, the receptacle having an interior and an opening into the interior; and
a protrusion member provided on the second member, the protrusion member having a size and shape suitable to be received at least partially in the opening of the receptacle of the third member;
wherein, upon moving the first member and the second member together, the protrusion member is received into the receptacle and the connection portion is received into the opening of the receptacle structure to cause the piercing end of the needle to pierce the septum to come into fluid flow communication with the interior chamber of the connection portion.

17. The delivery system of claim 1, the pierceable member including an interior volume extending along the longitudinal dimension of the needle.

18. The delivery system of claim 1, wherein the pierceable member has a U-shaped cross section.

19. A method of making a fluid delivery system, the method comprising:
providing a first member;
providing a receptacle structure on the first member and defining an interior chamber and an opening into the interior chamber;
supporting a needle within the interior chamber of the receptacle structure, the needle having a piercing end;
providing a pierceable member within the interior chamber, the pierceable member surrounding the piercing end of the needle;
providing a second member for connecting with the first member;
providing a connection portion on the second member, the connection portion having an interior chamber and an opening into the interior chamber of the connection portion, the connection portion having a size and shape suitable to be received at least partially into the opening of the receptacle structure as the first member and the second member are connected; and
supporting a septum by the connection portion of the second member in a position to cover the opening of the connection portion;
wherein the pierceable member is arranged to be moved, by the connection portion as the connection portion is received into the opening of the receptacle structure within the interior chamber of the receptacle structure in a direction along the longitudinal dimension of the needle toward the piercing end of the needle to cause the piercing end of the needle to pierce the pierceable member and the septum to establish fluid flow communication between the needle and the interior chamber of the connection portion;
wherein the receptacle structure is fixed with respect to a base portion; and
wherein the connection portion of the second member is provided in a housing that is connectable to the base portion.

20. A fluid delivery system, the fluid delivery system comprising:
a first member;
a receptacle structure provided on the first member and having an interior chamber and an opening into the interior chamber;
a needle supported within the interior chamber of the receptacle structure, the needle having a piercing end;
a second member for connecting with the first member, the second member comprising a reservoir for containing fluidic media, the reservoir including a connection portion having an interior chamber and an opening into the interior chamber of the connection portion, the connection portion having a size and shape suitable to be received at least partially into the opening of the receptacle structure as the first member and the second member are connected;
a septum supported by the connection portion of the second member in a position to cover the opening of the connection portion;
a groove provided in one of the receptacle structure and the connection portion; and
a protrusion arranged on the other of the receptacle structure and the connection portion to be insertable into the groove of the one of the receptacle structure and the connection portion as the opening of the receptacle structure receives the connection portion;
wherein, upon connecting the first member and the second member together, the protrusion is received into the groove and the connection portion is received into the opening of the receptacle structure to cause the piercing end of the needle to pierce the septum to establish fluid flow communication between the needle and the interior chamber of the connection portion of the reservoir;
wherein the protrusion extends in a same direction as the needle to engage the receptacle before the needle contacts the septum.

21. The fluid delivery system of claim 20, wherein the protrusion is arranged on the connection portion;
wherein the needle is arranged to extend out of the receptacle structure a first distance; and
wherein the protrusion includes a portion that extends from the connection portion a second distance greater than the first distance that the needle extends out of the receptacle structure.

22. The fluid delivery system of claim 21, wherein the protrusion is arranged on the connection portion such that the portion of the protrusion is received in the groove of the receptacle structure before the needle pierces septum.

23. The fluid delivery system of claim 21, the system further comprising:
a pierceable member provided within the interior chamber, adjacent the opening of the receptacle structuring, the pierceable member surrounding the end of the needle, the pierceable member arranged to extend out of the receptacle structure a third distance;
wherein the second distance that the portion of the protrusion extends from the connection portion is greater than the third distance that the pierceable member extends out of the receptacle structure; and wherein the protrusion is arranged on the connection portion such that the portion of the protrusion is insertable into the groove of the receptacle structure before the connection portion receives a portion of the pierceable member.

24. The fluid delivery system of claim 20, wherein the protrusion extends substantially along the connection portion of the reservoir.

25. The fluid delivery system of claim 20,
wherein the receptacle structure is fixed with respect to a base portion; and
wherein the connection portion of the second member is provided in a housing that is connectable to the base portion.

26. The fluid delivery system of claim 20, the structure further comprising:
a receptacle provided on a third member, the receptacle having an interior and an opening into the interior; and
a protrusion member provided on the second member, the protrusion member having a size and shape suitable to be received at least partially in the opening of the receptacle of the third member;
wherein, upon moving the first member and the second member together, the protrusion member is received into the receptacle and the connection portion is received into the opening of the receptacle structure to cause the piercing end of the needle to pierce the septum to come into fluid flow communication with the interior chamber of the connection portion.

27. The delivery system of claim 20, wherein the connection portion is configured for movement relative to the needle as the first member and the second member are connected.

28. The delivery system of claim 20, wherein the connection portion defines a port of the reservoir.

29. The delivery system of claim 20, wherein the protrusion is configured for movement relative to the needle as the first member and the second member are connected.

30. A method of manufacturing a fluid delivery device, the method comprising:
providing a first member;
providing a receptacle structure on the first member and having an interior chamber and an opening into the interior chamber;
providing a second member for connecting with the first member, the second member comprising a reservoir for containing fluidic media, the reservoir including a connection portion having an interior chamber and an opening into the interior chamber of the connection portion, the connection portion having a size and shape suitable to be received at least partially into the opening of the receptacle structure as the first member and the second member are connected;
providing a groove in one of the receptacle structure and the connection portion;
arranging a protrusion on the other of the receptacle structure and the connection portion to be insertable into the groove of the one of the receptacle structure and the connection portion as the opening of the receptacle structure receives the connection portion;
supporting a needle within the interior chamber of the receptacle structure, the needle having a piercing end; and
supporting a septum by the connection portion of the second member in a position to cover the opening of the connection portion;
wherein, upon connecting the first member and the second member together, the protrusion is received into the groove and the connection portion is received into the opening of the receptacle structure to cause the piercing end of the needle to pierce the septum to establish fluid flow communication between the needle and the interior chamber of the connection portion of the reservoir;
wherein the protrusion extends in a same direction as the needle to engage the receptacle before the needle contacts the septum.

31. A fluid delivery system, the fluid delivery system comprising:
a first member;
a receptacle structure provided on the first member and having an interior chamber and an opening into the interior chamber;
a needle supported within the interior chamber of the receptacle structure, the needle having a piercing end;
a second member for connecting with the first member, the second member comprising a reservoir for containing fluidic media supported by the second member, the reservoir having a connection portion, the connection portion having an interior chamber and an opening into the interior chamber of the connection portion, the connection portion having a size and shape suitable to be received at least partially in the opening of the receptacle structure as the first member and the second member are connected;
a further receptacle having an interior and an opening into the interior; and
a protrusion member provided on the second member, the protrusion member having a size and shape suitable to be received at least partially in the opening of the further receptacle;
wherein, upon connecting the first member and the second member together, the protrusion member is received into the further receptacle and the connection portion is received into the opening of the receptacle structure to cause the piercing end of the needle to pierce the septum to establish fluid flow communication between the needle and the interior chamber of the connection portion of the reservoir;
wherein the protrusion member is separate and apart from the connection portion of the reservoir.

32. The fluid delivery system of claim 31, wherein the connection portion of the reservoir comprises a port of the reservoir from which fluidic media is expelled.

33. The fluid delivery system of claim 31,
wherein the receptacle structure is fixed with respect to a base portion; and
wherein the connection portion of the second member is provided in a housing that is connectable to the base portion.

34. The fluid delivery system of claim 31,
wherein the second opening of the needle is provided in fluid flow communication with a needle injection site channel; and
wherein the needle injection site channel has an opening that is connectable to a needle inserting device for receiving at least a portion of a needle from the needle inserting device.

35. The fluid delivery system of claim 31,
wherein the receptacle structure is fixed with respect to a base portion;
wherein the connection portion of the second member is provided in a housing that is connectable to the base portion; and wherein the housing includes a recess through which a needle inserting device may extend when connected to the opening of the needle injection site channel.

36. The fluid delivery system of claim 31, the system further comprising:
   a pierceable member provided within the interior chamber, adjacent the opening of the receptacle structuring, the pierceable member surrounding the end of the needle, the pierceable member arranged to extend out of the receptacle structure a third distance;
   wherein the second distance that the portion of the protrusion extends from the connection portion is greater than the third distance that the pierceable member extends out of the receptacle structure; and
   wherein the protrusion is arranged on the connection portion such that the portion of the protrusion is insertable into the groove of the receptacle structure before the connection portion receives a portion of the pierceable member.

37. The delivery system of claim 31, further comprising:
   a third member for connecting with the first member and the second member;
   wherein the further receptacle is provided on the third member.

38. A fluid delivery system, comprising:
   a first member;
   a receptacle structure provided on the first member and having an interior chamber and an opening into the interior chamber;
   a needle supported within the interior chamber of the receptacle structure, the needle having a piercing end;
   a second member for connecting with the first member, the second member comprising a reservoir for containing fluidic media supported by the second member, the reservoir having a connection portion, the connection portion having an interior chamber and an opening into the interior chamber of the connection portion, the connection portion having a size and shape suitable to be received at least partially in the opening of the receptacle structure as the first member and the second member are connected;
   a receptacle having an interior and an opening into the interior; and
   a protrusion member provided on the second member, the protrusion member having a size and shape suitable to be received at least partially in the opening of the receptacle;
   wherein, upon connecting the first member and the second member together, the protrusion member is received into the receptacle and the connection portion is received into the opening of the receptacle structure to cause the piercing end of the needle to pierce the septum to establish fluid flow communication between the needle and the interior chamber of the connection portion of the reservoir; and
   wherein the protrusion member extends in a same direction as the needle to engage the receptacle before the needle contacts the septum.

39. A method of manufacturing an alignment system for aligning a first member in fluid flow connection with a second member, the method comprising:
   providing a first member;
   providing a receptacle structure on the first member and having an interior chamber and an opening into the interior chamber;
   supporting a needle within the interior chamber of the receptacle structure, the needle having a piercing end;
   providing a second member for connecting with the first member, the second member comprising a reservoir for containing fluidic media supported by the second member, the reservoir having a connection portion, the connection portion having an interior chamber and an opening into the interior chamber of the connection portion, the connection portion having a size and shape suitable to be received at least partially in the opening of the receptacle structure as the first member and the second member are connected;
   providing a further receptacle having an interior and an opening into the interior; and
   providing a protrusion member on the second member, the protrusion member having a size and shape suitable to be received at least partially in the opening of the further receptacle;
   wherein, upon connecting the first member and the second member together, the protrusion member is received into the further receptacle and the connection portion is received into the opening of the receptacle structure to cause the piercing end of the needle to pierce the septum to establish fluid flow communication between the needle and the interior chamber of the connection portion of the reservoir; and
   wherein the protrusion member is separate and apart from the connection portion of the reservoir.

\* \* \* \* \*